(12) United States Patent
Okazaki et al.

(10) Patent No.: US 10,252,106 B2
(45) Date of Patent: Apr. 9, 2019

(54) GOLF SWING ANALYSIS APPARATUS AND GOLF CLUB FITTING APPARATUS

(71) Applicants: DUNLOP SPORTS CO. LTD., Kobe-shi, Hyogo (JP); SUMITOMO RUBBER INDUSTRIES, LTD., Kobe-shi, Hyogo (JP)

(72) Inventors: Kousuke Okazaki, Kobe (JP); Masahiko Ueda, Kobe (JP); Masatoshi Kato, Kobe (JP); Yuki Nagano, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 428 days.

(21) Appl. No.: 14/743,625

(22) Filed: Jun. 18, 2015

(65) Prior Publication Data
US 2015/0367174 A1    Dec. 24, 2015

(30) Foreign Application Priority Data

Jun. 19, 2014 (JP) .................................. 2014-126560
Jun. 19, 2014 (JP) .................................. 2014-126561
Nov. 21, 2014 (JP) .................................. 2014-237115

(51) Int. Cl.
*A63B 67/02* (2006.01)
*A63B 69/36* (2006.01)
(Continued)

(52) U.S. Cl.
CPC ............ *A63B 24/0003* (2013.01); *A61B 5/11* (2013.01); *A61B 5/6895* (2013.01); *G06K 9/00342* (2013.01)

(58) Field of Classification Search
USPC ................ 473/118, 131, 223, 226, 247, 409
See application file for complete search history.

(56) References Cited

U.S. PATENT DOCUMENTS 6,537,076 B2 * 3/2003 McNitt ............. A63B 24/0003
434/247
8,944,939 B2 * 2/2015 Clark ...................... G01P 13/00
463/36

(Continued)

FOREIGN PATENT DOCUMENTS

JP     2013-226375 A     12/2013
JP     2014-073314 A      4/2014
JP      2015-8881 A       1/2015

OTHER PUBLICATIONS

Japanese Notification of Reasons for Rejection for Japanese Application No. 2014-126560, dated Mar. 6, 2018, with an English translation.

*Primary Examiner* — Nini Legesse
(74) *Attorney, Agent, or Firm* — Birch, Stewart, Kolasch & Birch, LLP

(57) ABSTRACT

A golf swing analysis apparatus for analyzing a swing action of a golf club is provided. The golf swing analysis apparatus comprises an acquisition unit configured to acquire a measurement value obtained by measuring the swing action using a measurement device; a grip behavior derivation unit configured to derive a behavior of a grip of the golf club that occurs during the swing action, based on the measurement value; and a shoulder behavior derivation unit configured to derive a behavior of a pseudo shoulder of a golfer that occurs during the swing action, based on the behavior of the grip.

13 Claims, 25 Drawing Sheets

(51) Int. Cl.
 *A63B 24/00* (2006.01)
 *G06K 9/00* (2006.01)
 *A61B 5/00* (2006.01)
 *A61B 5/11* (2006.01)

(56) References Cited

U.S. PATENT DOCUMENTS

| | | | |
|---|---|---|---|
| 2006/0025229 A1* | 2/2006 | Mahajan | A63B 24/0003 473/131 |
| 2010/0204616 A1* | 8/2010 | Shears | A61B 5/1124 600/595 |
| 2013/0065711 A1* | 3/2013 | Ueda | A61B 5/6895 473/409 |
| 2013/0260923 A1 | 10/2013 | Okazaki et al. | |
| 2014/0100048 A1 | 4/2014 | Ota et al. | |
| 2014/0100049 A1 | 4/2014 | Ota et al. | |
| 2014/0100050 A1 | 4/2014 | Ota et al. | |
| 2014/0342844 A1* | 11/2014 | Mooney | G06K 9/00342 473/266 |

* cited by examiner

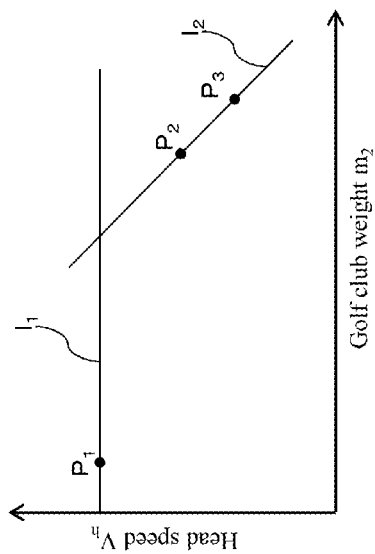
Fig.20A
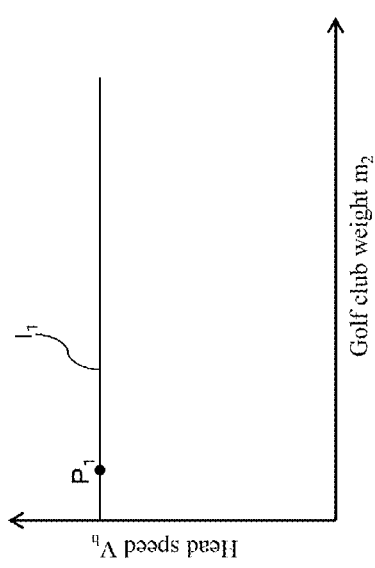
Fig.20C
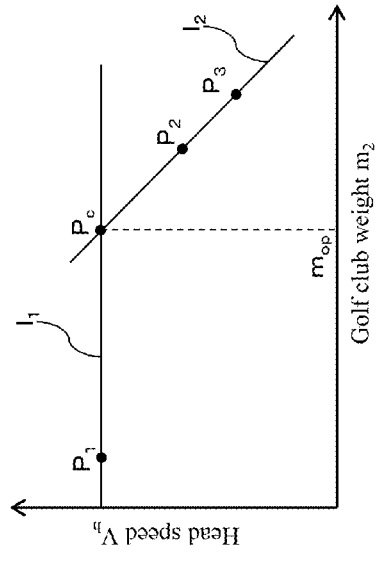
Fig.20B
Fig.20D

GOLF SWING ANALYSIS APPARATUS AND GOLF CLUB FITTING APPARATUS

CROSS REFERENCE TO RELATED APPLICATIONS

This application claims priorities to Japanese Patent Applications No. 2014-126560 filed on Jun. 19, 2014, No. 2014-126561 filed on Jun. 19, 2014, and No. 2014-237115 filed on Nov. 21, 2014, which are hereby incorporated by reference in their entirety.

FIELD OF INVENTION

The present invention relates to a golf swing analysis apparatus, a golf swing analysis method and a golf swing analysis program that analyze the swing action of a golf club, and to a golf club fitting apparatus, method and program.

BACKGROUND

Heretofore, various analysis techniques for analyzing the swing action of a golf club have been proposed in order to help in golf club fitting, golf club product development, improving a golfer's swing action, and the like. In many cases, this type of golf swing analysis involves measuring the swing action with a measurement device such as an acceleration sensor, an angular velocity sensor or a camera, and deriving the behavior of the golf club that occurs during the swing action based on the measurement values.

In analyzing the swing action, the behavior of the golf club may be modeled with the dynamic model of a double pendulum. For example, the behavior of the club can be represented with a model that takes the golfer's shoulder and the grip of the club (or the wrist of the golfer holding the grip) as nodes, and takes the golfer's arm and the golf club as links. Also, Patent Literature 1 (JP 2014-73314A) discloses a double pendulum model that takes the middle of both shoulders of the golfer and the grip as nodes.

In Patent Literature 1, in order to model the swing action with a double pendulum model, an inertial sensor is attached the golfer's upper body and the movement of the upper body is measured, and an inertial sensor is also attached to the golf club and the movement of the golf club is measured. However, when the measurement device is thus attached to various sites to measure the movement of the various sites in order to analyze the swing action with a double pendulum model, the measurement device becomes large scale. Attaching the measurement device to the golfer's body, particularly as in Patent Literature 1, impedes the golfer's natural movement, possibly resulting in less accurate analysis.

Also, various fitting methods for assisting selection of golf clubs suited to a golfer have heretofore been proposed. A typical fitting method involves getting the golfer to take practice hits with the golf clubs, measuring the swing action during this time with a measurement apparatus, and analyzing the measurement values to thereby select an optimal golf club. The criteria on which fitting is based at this time is an important factor in determining the quality of the fitting, with various criteria having been proposed to date. For example, Patent Literature 2 (JP 2013-226375A) discloses a fitting method that is based on the stiffness of the shaft of the golf club.

SUMMARY OF INVENTION

Although the ease with which a golf club is swung, that is, the swingability of the golf club, may serve as one fitting criterion in selecting golf clubs, it is not the case that the easier a club is to swing the better the club. For example, the lighter the club the easier it is to swing, but there is also a decrease in the kinetic energy that is transferred to the ball by the impact with the club, and carry distance stops increasing. Having said that, if the club is too heavy it becomes difficult to swing, and carry distance stops increasing.

One object of the present invention is to provide a golf swing analysis apparatus, a golf swing analysis method and a golf swing analysis program that enable the swing action of a golf club to be modeled with a double pendulum model, without using a large-scale measurement device.

Also, another object of the present invention is to provide a golf club fitting apparatus, method and program that are able to specify an optimal swingability for a golfer.

A golf swing analysis apparatus according to aspect A1 is for analyzing a swing action of a golf club and includes an acquisition unit configured to acquire a measurement value obtained by measuring the swing action using a measurement device, a grip behavior derivation unit configured to derive a behavior of a grip of the golf club that occurs during the swing action, based on the measurement value, and a shoulder behavior derivation unit configured to derive a behavior of a pseudo shoulder of a golfer that occurs during the swing action, based on the behavior of the grip.

Here, the swing action is analyzed, based on a double pendulum model that takes the grip of the golf club and the golfer's shoulder as nodes. More specifically, the behavior of these two nodes consisting of the grip and the shoulder is specified in order to define such a double pendulum model. The behavior of the grip is derived based on the values measured by the measurement device. On the other hand, the behavior of the shoulder is derived as the behavior of pseudo shoulder, based on the behavior of the grip. That is, (values measured by) a separate measurement device need not necessarily be used in order to derive the behavior of the shoulder. Accordingly, the swing action of a golf club can be modeled with a double pendulum model, without using (values measured by) a large-scale measurement device.

A golf swing analysis apparatus according to aspect A2 of the present invention is the golf swing analysis apparatus according to aspect A1 in which the grip behavior derivation unit is configured to derive a grip velocity and a grip angular velocity. Also, the shoulder behavior derivation unit is configured to calculate an angular velocity of an arm of the golfer, based on the grip velocity.

Here, the grip velocity and the grip angular velocity are derived in order to specify the behavior of the grip. Also, the angular velocity of the golfer's arm representing the behavior of the shoulder is derived, based on the grip velocity. That is, the behavior of the two nodes consisting of the grip and the shoulder is specified by the grip angular velocity and the angular velocity of the golfer's arm.

A golf swing analysis apparatus according to aspect A3 of the present invention is the golf swing analysis apparatus according to aspect A1 or A2 in which the shoulder behavior derivation unit is configured to derive the behavior of the pseudo shoulder, under an assumption that the grip circulates about the shoulder and the shoulder does not move during the swing action.

Here, a double pendulum model in which the grip circulates about the stationary (but rotatable) shoulder is employed. Accordingly, the double pendulum model can be defined in a simple manner.

A golf swing analysis apparatus according to aspect A4 of the present invention is the golf swing analysis apparatus according to any of aspects A1 to A3 in which the grip behavior derivation unit is configured to derive the behavior of the grip in a global coordinate system, and transform the derived behavior of the grip into a behavior in a swing plane. Also, the shoulder behavior derivation unit is configured to derive the behavior of the pseudo shoulder in the swing plane, based on the behavior of the grip in the swing plane.

Here, the double pendulum model is defined in a swing plane. That is, the double pendulum model can be defined in a simple manner.

A golf swing analysis apparatus according to aspect A5 of the present invention is the golf swing analysis apparatus according to any of aspects A1 to A4 in which the acquisition unit is configured to acquire the measurement value of the swing action measured by an acceleration sensor and an angular velocity sensor attached to the golf club that serve as the measurement device.

Here, the behavior of the grip can be specified, based on the acceleration sensor and the angular velocity sensor attached to the golf club.

A golf swing analysis apparatus according to aspect A6 of the present invention is the golf swing analysis apparatus according to aspect A5 in which the acquisition unit is configured to further acquire the measurement value of the swing action measured by a geomagnetic sensor attached to the golf club that serves as the measurement device.

Here, the behavior of the grip can be specified, based on a geomagnetic sensor that is similarly attached to the golf club, in addition to the acceleration sensor and the angular velocity sensor that are attached to the golf club.

A golf swing analysis apparatus according to aspect A7 of the present invention is the golf swing analysis apparatus according to any of aspects A1 to A6 further including an index calculation unit configured to calculate at least one of a head speed, a torque exertion amount, an average torque, an average power and an energy exertion amount, as a swing index characterizing the swing action, based on the behavior of the grip and the behavior of the pseudo shoulder.

Here, at least one of head speed, torque exertion amount, average torque, average power and energy exertion amount is calculated, based on the behavior of the grip and the behavior of the pseudo shoulder, as a swing index characterizing the swing action. Accordingly, the swing action can be evaluated based on at least one of head speed, torque exertion amount, average torque, average power, and energy exertion amount.

A golf swing analysis apparatus according to aspect A8 of the present invention is the golf swing analysis apparatus according to aspect A7 in which the index calculation unit is configured to calculate a value of a wrist-cock release timing that occurs during the swing action, the average power and/or the energy exertion amount, based on the behavior of the grip and the behavior of the pseudo shoulder, and calculate the head speed that occurs at a time of impact as the swing index, in accordance with a predetermined regression equation that uses the wrist-cock release timing, the average power and/or the energy exertion amount as explanatory variables.

The inventors found that the wrist-cock release timing during the swing action, the average power and/or the energy exertion amount are correlated with the head speed at the time of impact. In view of this, first, the values of the wrist-cock release timing, the average power and/or the energy exertion amount are calculated here, in accordance with the double pendulum model. The head speed at the time of impact is then calculated, based on a predetermined regression equation that uses these values as explanatory variables. Accordingly, the head speed at the time of impact can be calculated with high accuracy, therefore enabling the swing action to be evaluated with high accuracy.

A golf swing analysis method according to aspect A9 of the present invention is for analyzing a swing action of a golf club and includes the steps of measuring the swing action using a measurement device, deriving a behavior of a grip of the golf club that occurs during the swing action, based on a measurement value of the swing action, and deriving a behavior of a pseudo shoulder of a golfer that occurs during the swing action, based on the behavior of the grip. Here, similar effects to aspect 1 can be achieved.

A golf swing analysis program stored in a non-transitory computer readable medium according to aspect A10 of the present invention is for analyzing a swing action of a golf club and causes a computer to execute the steps of acquiring a measurement value obtained by measuring the swing action using a measurement device, deriving a behavior of a grip of the golf club that occurs during the swing action, based on the measurement value, and deriving a behavior of a pseudo shoulder of a golfer that occurs during the swing action, based on the behavior of the grip. Here, similar effects to aspect 1 can be achieved.

Incidentally, the inventors found that a relationship such as roughly shown in FIGS. 13A and 13B exists between predetermined swing indices such as head speed and torque exertion amount and the swingability of the golf club such as the weight of the club and the moment of inertia about the grip end. For example, as the club becomes heavier, the golfer becomes unable to freely swing the golf club and head speed decreases. Having said that, head speed plateaus after the weight of the club drops to a certain level (see FIG. 13A). This is because the club cannot be swung at greater than the power used for a full swing. On the other hand, the torque exertion amount during the swing increases as the golf club becomes heavier, but when the weight of the club increases to a certain level, the golfer reaches his or her limits and the torque exertion amount plateaus (see FIG. 13B). That is, the swing indices stop increasing if the golfer has reached his or her limits, even if the club is made easier to swing or harder to swing. Aspects B1 to B9 of the present invention constitute an invention that is based on these findings.

A golf club fitting apparatus according to aspect B1 of the present invention includes an acquisition unit, an index calculation unit, and an optimal index specification unit. The acquisition unit is configured to acquire a measurement value obtained by measuring a swing action taken with each of a plurality of golf clubs. The index calculation unit is configured to calculate a swing index, which is an index characterizing the swing action, for each of the golf clubs, based on the measurement value. The optimal index specification unit is configured to specify an intersection point between a first regression line and a second regression line, based on the swing indices calculated by the index calculation unit, and specify one of an optimal index, which is the swingability index at or near the intersection point, and an optimal index range. The first regression line is a regression line of the swing index in a constant region where the swing index is roughly constant relative to the swingability index. The second regression line is a regression line of the swing index in a proportional region where the swing index is roughly proportional to the swingability index.

Here, the swingability index at or near the intersection point between the first regression line of the swing index in the constant region and the second regression line of the swing index in the proportional region such as shown in FIGS. 13A and 13B is specified. This intersection point is a point (changing point in FIGS. 13A and 13B) corresponding to the golfer's limits at which the swing index stops increasing even if the golf club becomes easier to swing or harder to swing. Accordingly, here, an optimal swingability index that realizes an optimal swing index corresponding to the golfer's limits is specified. That is, the optimal swingability for the golfer can be specified.

A golf club fitting apparatus according to aspect B2 of the present invention is the fitting apparatus of the golf club according to aspect B1 in which the acquisition unit is configured to acquire a first measurement value obtained by measuring the swing action of a golf club having an extremely small swingability index, and a second measurement value obtained by measuring the swing action of a golf club having an extremely large swingability index. Also, the optimal index specification unit is configured to specify the first regression line, based on the swing index that is based on the first measurement value, and the second regression line, based on the swing index that is based on the second measurement value, or specify the first regression line, based on the swing index that is based on the second measurement value, and the second regression line, based on the swing index that is based on the first measurement value.

As shown in FIGS. 13A and 13B, the swing index is divided, at a certain point, into a proportional region in which the swing index is proportional to the swingability index and a constant region in which the swing index is roughly constant regardless of the swingability index. Accordingly, the measurement value of the swing action resulting from a golf club having an extremely small swingability index (first measurement value) and the measurement value of the swing action resulting from a golf club having an extremely large swingability index (second measurement value) will normally belong separately to either the constant region or the proportional region. Here, based on these findings, one of the first regression line and the second regression line is specified based on the first measurement value, and the other of the first regression line and the second regression line is specified based on the second measurement value. As a result, the first regression line and the second regression line can be specified with a small number of practice hits.

Note that although a relationship between the swing index and the swingability index is as shown as FIGS. 13A and 13B, it is thought that there is in fact a region near the changing point where change is gradual. Less accurate analysis may result from specifying the constant region and the proportional region based on values measured in such a region where change is gradual. However, here, measurement values resulting from a golf club having an extremely small swingability index and a golf club having an extremely large swingability index are used, as mentioned above, thus enabling such problems to be avoided.

A golf club fitting apparatus according to aspect B3 of the present invention is the fitting apparatus of the golf club according to aspect B1 or B2 in which the optimal index specification unit is configured to specify the first regression line as a straight line that has a zero slope and passes through a point corresponding to the swing index that is based on the measurement value from one golf club.

Here, the first regression line can be specified by only taking practice hits with one golf club.

A golf club fitting apparatus according to aspect B4 of the present invention is the fitting apparatus of the golf club according to any of aspects B1 to B3 in which the optimal index specification unit is configured to specify the second regression line, based on a regression equation of a slope of the second regression line that uses at least one of a wrist-cock release timing at a time of the swing action and a head speed at a time of impact as an explanatory variable.

The inventors found that the slope (proportionality constant in the proportional region) of the second regression line is correlated with the wrist-cock release timing during the swing action and/or the head speed at the time of impact. In view of this, here, the slope of the second regression line is calculated based on at least one of the wrist-cock release timing during the swing action and the head speed at the time of impact. Accordingly, the second regression line can be specified with a small number of practice hits.

A golf club fitting apparatus according to aspect B5 of the present invention is the fitting apparatus of the golf club according to aspect B4 in which the optimal index specification unit is configured to specify the second regression line as a straight line that has the slope calculated based on the regression equation and passes through a point corresponding to the swing index that is based on the measurement value from one golf club.

Here, the second regression line can be specified by only taking practice hits with one golf club.

A golf club fitting apparatus according to aspect B6 of the present invention is the fitting apparatus of the golf club according to one of aspects B1 to B5 in which at least one of a weight of the golf club, a moment of inertia about a grip end of the golf club and a moment of inertia about a shoulder of a golfer is included in the swingability index.

Here, the swingability of the golf club is evaluated, based on at least one of the weight of the golf club, the moment of inertia about the grip end, and the moment of inertia about the golfer's shoulder.

A golf club fitting apparatus according to aspect B7 of the present invention is the fitting apparatus of the golf club according to one of aspects B1 to B6 in which at least one of a head speed, a torque exertion amount, an average torque, an average power and an energy exertion amount is included in the swing index.

Here, the swing index is evaluated based on at least one of head speed, torque exertion amount, average torque, average power, and energy exertion amount.

A golf club fitting apparatus according to aspect B8 of the present invention is the fitting apparatus of the golf club according to one of aspects B1 to B7 further including an optimal club specification unit configured to specify a golf club having a small swing moment of inertia and a large grip end moment of inertia, from among a plurality of golf clubs that match the optimal index or the optimal index range.

Here, a golf club that can even more increase head speed can be specified from among a plurality of golf clubs that match an optimal index or an optimal index range.

A golf club fitting method according to aspect B9 of the present invention includes the following steps. Here, similar effects to aspect 1 can be achieved. These steps are:

(1) a step of measuring a swing action taken with each of a plurality of golf clubs using a measurement device;

(2) a step of calculating a swing index, which is an index characterizing the swing action, for each of the golf clubs, based on a measurement value of the swing action;

(3) a step of specifying a first regression line of the swing index in a constant region in which the swing index is roughly constant relative to a swingability index representing an ease of swinging the golf club, based on the calculated swing index;

(4) a step of specifying a second regression line of the swing index in a proportional region in which the swing index is roughly proportional to the swingability index, based on the calculated swing index; and (5) a step of specifying an intersection point between the first regression line and the second regression line, and specifying one of an optimal index, which is the swingability index at or near the intersection point, and an optimal index range.

A golf club fitting method according to aspect B10 of the present invention is the golf club fitting method according to aspect B9 further including the following step. Here, similar effects to aspect 8 can be achieved. This step is:

(6) a step of specifying a golf club having a small swing moment of inertia and a large grip end moment of inertia, from among a plurality of golf clubs that match the optimal index or the optimal index range.

A golf club fitting program stored in a non-transitory computer readable medium according to aspect B11 of the present invention causes a computer to execute the following steps. Here, similar effects to aspect 1 can be achieved. These steps are:

(1) a step of acquiring a measurement value obtained by measuring a swing action taken with each of a plurality of golf clubs;

(2) a step of calculating a swing index, which is an index characterizing the swing action, for each of the golf clubs, based on the measurement value;

(3) a step of specifying a first regression line of the swing index in a constant region in which the swing index is roughly constant relative to a swingability index representing an ease of swinging the golf club, based on the calculated swing index;

(4) a step of specifying a second regression line of the swing index in a proportional region in which the swing index is roughly proportional to the swingability index, based on the calculated swing index; and (5) a step of specifying an intersection point between the first regression line and the second regression line, and specifying one of an optimal index, which is the swingability index at or near the intersection point, and an optimal index range.

A golf club fitting program stored in a non-transitory computer readable medium according to aspect B12 of the present invention is the fitting apparatus of the golf club according to aspect B11 further causing the computer to execute the following step. Here, similar effects to aspect 8 can be achieved. This step is:

(6) a step of specifying a golf club having a small swing moment of inertia and a large grip end moment of inertia, from among a plurality of golf clubs that match the optimal index or the optimal index range.

According to aspect A1 of the present invention, the swing action of a golf club can be modeled with a double pendulum model, without using (values measured by) a large-scale measurement device. According to aspect B1 of the present invention, an optimal swingability index that realizes an optimal swing index corresponding to the golfer's limits is specified. That is, the optimal swingability for a golfer can be specified.

BRIEF DESCRIPTION OF DRAWINGS

FIGS. 20A to 20D are diagrams illustrating an optimal index specification process;

DETAILED DESCRIPTION OF THE PREFERRED EMBODIMENTS

Hereinafter, a golf swing analysis apparatus, a golf swing analysis method and a golf swing analysis program according to one embodiment (first embodiment) of the present invention will be described, followed by description of a golf club fitting apparatus, method and program according to another embodiment (second embodiment) of the present invention, with reference to the drawings.

1. First Embodiment 1-1. Schematic Configuration of Golf Swing Analysis System

Figure 1:
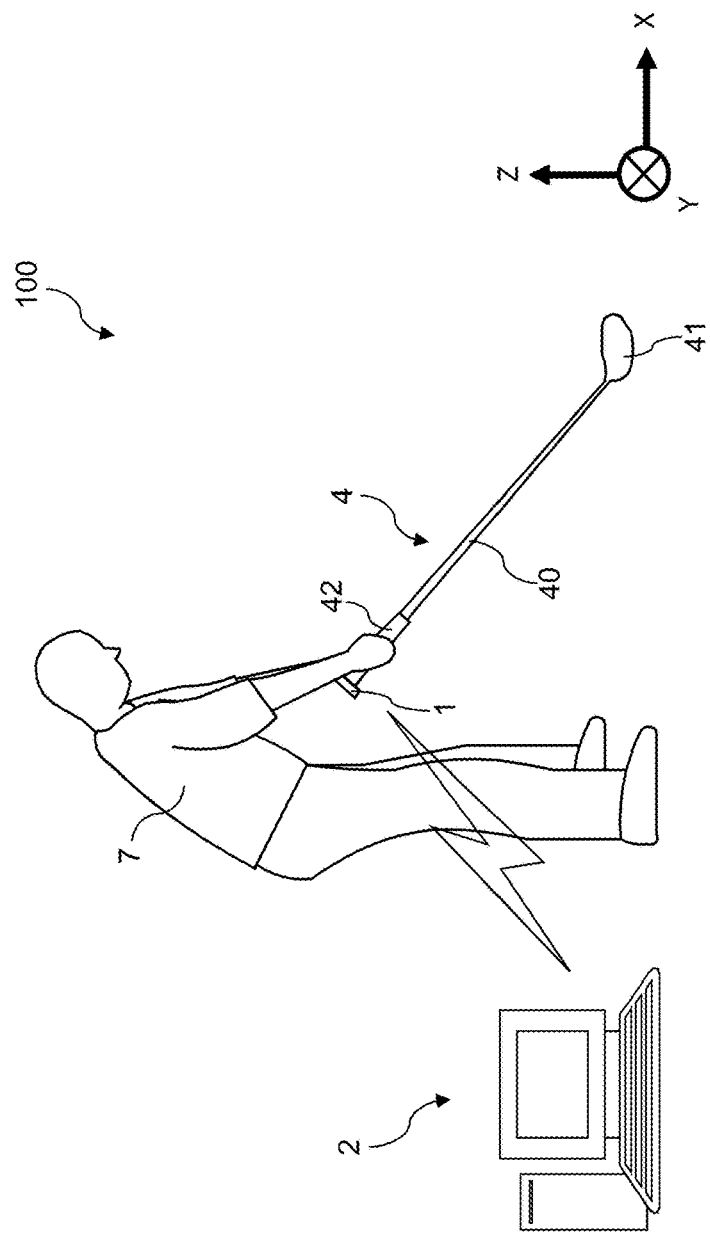
FIG. 1 is a diagram showing a golf swing analysis system provided with a golf swing analysis apparatus according to one embodiment of the present invention.
Figure 2:
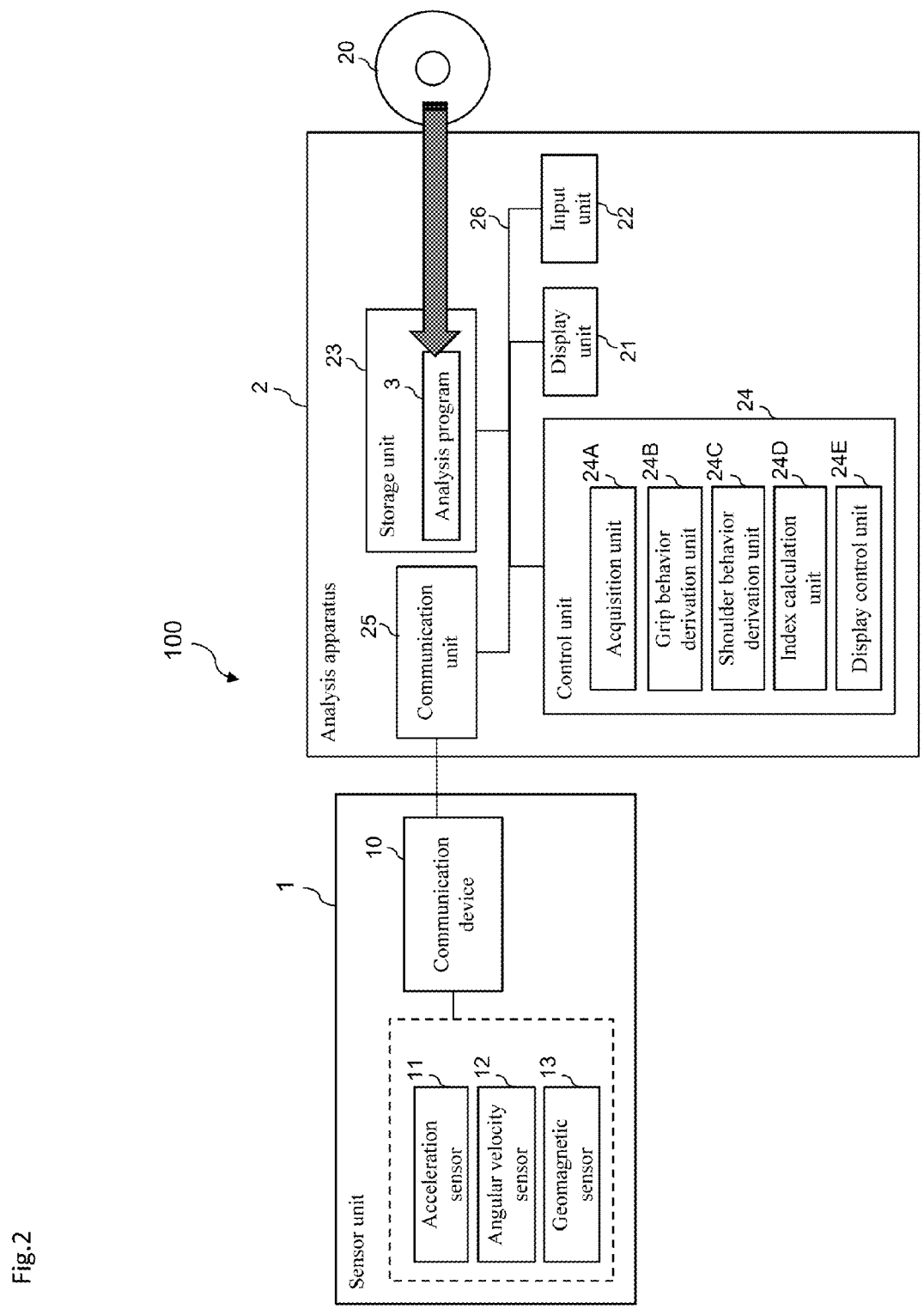
FIG. 2 is a functional block diagram of the golf swing analysis system.

FIGS. 1 and 2 show the overall configuration of a golf swing analysis system (hereinafter, analysis system 100) that is provided with a golf swing analysis apparatus (hereinafter, analysis apparatus 2) according to the present embodiment. The analysis apparatus 2 analyzes the swing action of a golf club 4, based on measurement data obtained by measuring the swing action of the golf club 4 by a golfer 7. In the present embodiment, the analysis apparatus 2 is applied to assisting fitting of the golf club 4. The swing action is measured by a sensor unit 1 (measurement device) attached to a grip 42 of the golf club 4, and the analysis apparatus 2 together with the sensor unit 1 constitutes the analysis system 100.

Hereinafter, the configuration of the sensor unit 1 and the analysis apparatus 2 will be described, followed by description of the flow of swing action analysis processing.

1-1-1. Configuration of Sensor Unit

Figure 3:
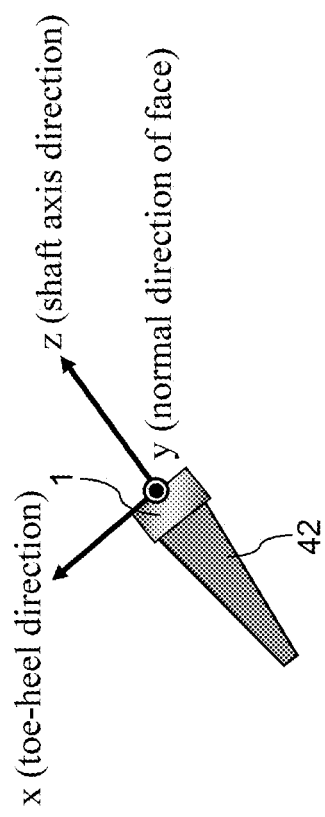
FIG. 3 is a diagram illustrating an xyz local coordinate system that is based on the grip of a golf club.

The sensor unit 1 is, as is shown in FIGS. 1 and 3, attached to an end portion (grip end) of the grip 42 of the golf club 4 on the opposite side to a head 41, and measures the behavior of the grip 42. Note that the golf club 4 is a common golf club, and is constituted by a shaft 40, the head 41 provided at one end of the shaft 40, and the grip 42 provided at the other end of the shaft 40. The sensor unit 1 is configured to be small and lightweight so as to not impede the swing action. As shown in FIG. 2, an acceleration sensor 11, an angular velocity sensor 12 and a geomagnetic sensor 13 are mounted in the sensor unit 1 according to the present embodiment. Also, a communication device 10 for transmitting measurement data that is measured by these sensors 11 to 13 to the external analysis apparatus 2 is also mounted in the sensor unit 1. Note that, in the present embodiment, the communication device 10 is a wireless communication device so as to not impede the swing action, but may be configured to be connected to the analysis apparatus 2 via a cable in a wired manner.

The acceleration sensor 11, the angular velocity sensor 12, and the geomagnetic sensor 13 respectively measure grip acceleration, grip angular velocity and grip geomagnetism in an xyz local coordinate system that is based on the grip 42. More specifically, the acceleration sensor 11 measures grip accelerations $a_x$, $a_y$ and $a_z$ in the x-axis, y-axis and z-axis directions. The angular velocity sensor 12 measures grip angular velocities $\omega_x$, $\omega_y$ and $\omega_z$ about the x-axis, the y-axis, and the z-axis. The geomagnetic sensor 13 measures grip geomagnetisms $m_x$, $m_y$ and $m_z$ in the x-axis, y-axis and z-axis directions. These measurement data are acquired as time-series data at a predetermined sampling period $\Delta t$. Note that the xyz local coordinate system is a three-axis orthogonal coordinate system defined as shown in FIG. 3. That is, the z-axis coincides with the direction in which the shaft 40 extends, and the direction from the head 41 toward the grip 42 is the z-axis positive direction. The x-axis is oriented so as to be aligned as closely as possible with the toe-heel direction of the head 41, and the y-axis is oriented so as to be aligned as closely as possible with the normal direction of the face of the head 41.

In the present embodiment, the measurement data measured by the acceleration sensor 11, the angular velocity sensor 12, and the geomagnetic sensor 13 is transmitted to the analysis apparatus 2 via the communication device 10 in real time. However, a configuration may, for example, be adopted in which the measurement data is stored in a storage device within the sensor unit 1, and, after the end of the swing action, the measurement data is retrieved from the storage device and delivered to the analysis apparatus 2.

1-1-2. Configuration of Analysis Apparatus

The configuration of the analysis apparatus 2 will be described with reference to FIG. 2. The analysis apparatus 2 is manufactured by installing a golf swing analysis program (hereinafter, analysis program 3) according to the present embodiment that is stored in a computer readable recording medium 20 such as a CD-ROM or a USB memory on a general-purpose personal computer from the recording medium 20. The analysis program 3 is software for analyzing swing action based on measurement data sent from the sensor unit 1, and outputting information that assists the selection of golf clubs suited to the golfer 7. The analysis program 3 causes the analysis apparatus 2 to execute operations which will be discussed later.

The analysis apparatus 2 is provided with a display unit 21, an input unit 22, a storage unit 23, a control unit 24, and a communication unit 25. These units 21 to 25 are connected via a bus line 26, and can communicate with each other. In the present embodiment, the display unit 21 is constituted by a liquid crystal display or the like, and displays information which will be discussed later to a user. Note that a user as referred to here is a general term for persons that require fitting results such as the golfer 7 or his or her instructor. Also, the input unit 22 can be constituted by a mouse, a keyboard, a touch panel or the like, and accept operations to the analysis apparatus 2 from the user.

The storage unit 23 is constituted by a non-volatile storage device such as a hard disk. Measurement data sent from the sensor unit 1 is saved to the storage unit 23, in addition to the analysis program 3 being stored therein. The communication unit 25 is a communication interface that enables communication between the analysis apparatus 2 and an external device, and receives data from the sensor unit 1.

The control unit 24 can be constituted by a CPU, a ROM, a RAM, and the like. The control unit 24 operates in a virtual manner as an acquisition unit 24A, a grip behavior derivation unit 24B, a shoulder behavior derivation unit 24C, an index calculation unit 24D, and a display control unit 24E, by reading out and executing the analysis program 3 stored in the storage unit 23. The operations of each of the units 24A to 24E will be discussed in detail later.

1-2. Analysis Processing of Swing Action

Next, swing action analysis processing that is performed by the analysis system 100 and is for mainly fitting the golf club 4 will be described. The analysis processing according to the present embodiment is constituted by the following six processes.

(1) A measurement process of measuring measurement data of grip accelerations $a_x$, $a_y$ and $a_z$, grip angular velocities $\omega_x$, $\omega_y$ and $\omega_z$, and grip geomagnetisms $m_x$, $m_y$ and $m_z$ in the xyz local coordinate system.

(2) A first transformation process of transforming the measurement data of the xyz local coordinate system obtained with the measurement process into grip accelerations $a_X$, $a_Y$ and $a_Z$ and grip angular velocities $\omega_X$, $\omega_Y$ and $\omega_Z$ in an XYZ global coordinate system (in the first transformation process, grip velocities $v_X$, $v_Y$ and $v_Z$ in the XYZ global coordinate system are also derived).

(3) A second transformation process of transforming the behavior of the grip 42 in the XYZ global coordinate system (grip angular velocities $\omega_X$, $\omega_Y$, $\omega_Z$ and grip velocities $v_X$, $v_Y$ and $v_Z$) into the behavior of the grip 42 in a swing plane P (discussed later).

(4) A shoulder behavior derivation process of deriving the behavior of pseudo shoulder of the golfer 7 in swing plane P, based on the behavior of the grip 42 in swing plane P.

(5) An index calculation process of calculating a swing index characterizing the swing action, based on the behavior of the grip 42 and the behavior of the pseudo shoulder.

(6) An output process of outputting the swing index and information obtained by further processing the swing index.

Hereinafter, these processes will be described in the above order.

Note that the XYZ global coordinate system is a three-axis orthogonal coordinate system defined as shown in FIG. 1. That is, the Z-axis extends vertically upward from below, the X-axis extends from the back of the golfer 7 toward his or her abdomen, and the Y-axis extends in a direction from the ball hitting point toward the target point in parallel to a horizontal plane.

1-2-1. Measurement Process

In the measurement process, the golfer 7 swings the golf club 4 having the sensor unit 1. The measurement data of grip accelerations $a_x$, $a_y$, and $a_z$, grip angular velocities $\omega_x$, $\omega_y$, and $\omega_z$, and grip geomagnetisms $m_x$, $m_y$, and $m_z$ during this swing are then measured by the sensor unit 1. This measurement data is transmitted to the analysis apparatus 2 via the communication device 10 of the sensor unit 1. On the other hand, in the analysis apparatus 2, the acquisition unit 24A receives the measurement data via the communication unit 25, and stores the received measurement data in the storage unit 23. In the present embodiment, time-series measurement data at least from address to impact is measured.

Figure 4D:
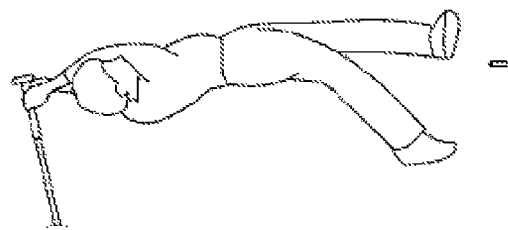
FIG. 4D is a diagram showing a finish state.
Figure 4C:
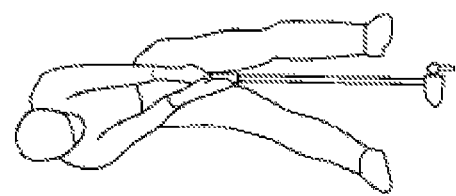
FIG. 4C is a diagram showing an impact state.
Figure 4B:
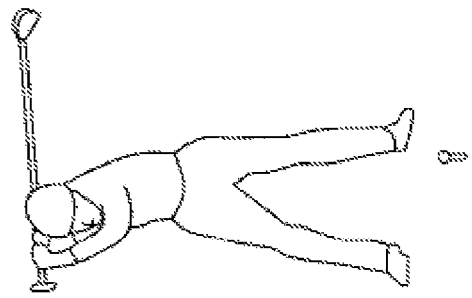
FIG. 4B is a diagram showing a top state.
Figure 4A:
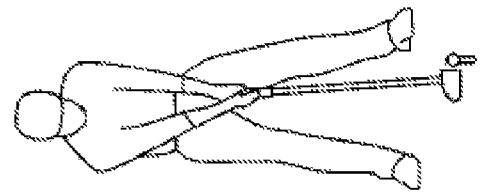
FIG. 4A is a diagram showing an address state.

Note that generally the swing action of a golf club proceeds in order of address, top, impact, and finish. The address refers to an initial state where the head 41 of the golf club 4 is disposed near the ball, as shown in FIG. 4A, and the top refers to a state where the golf club 4 is taken away from the address and the head 41 is swung up to its highest position, as shown in FIG. 4B. The impact refers to a state at the moment where the golf club 4 is swung down from the top and the head 41 impacts the ball, as shown in FIG. 4C, and the finish refers to a state where the golf club 4 is swung through to the front after the impact, as shown in FIG. 4D.

1-2-2. First Transformation Process

Figure 5:
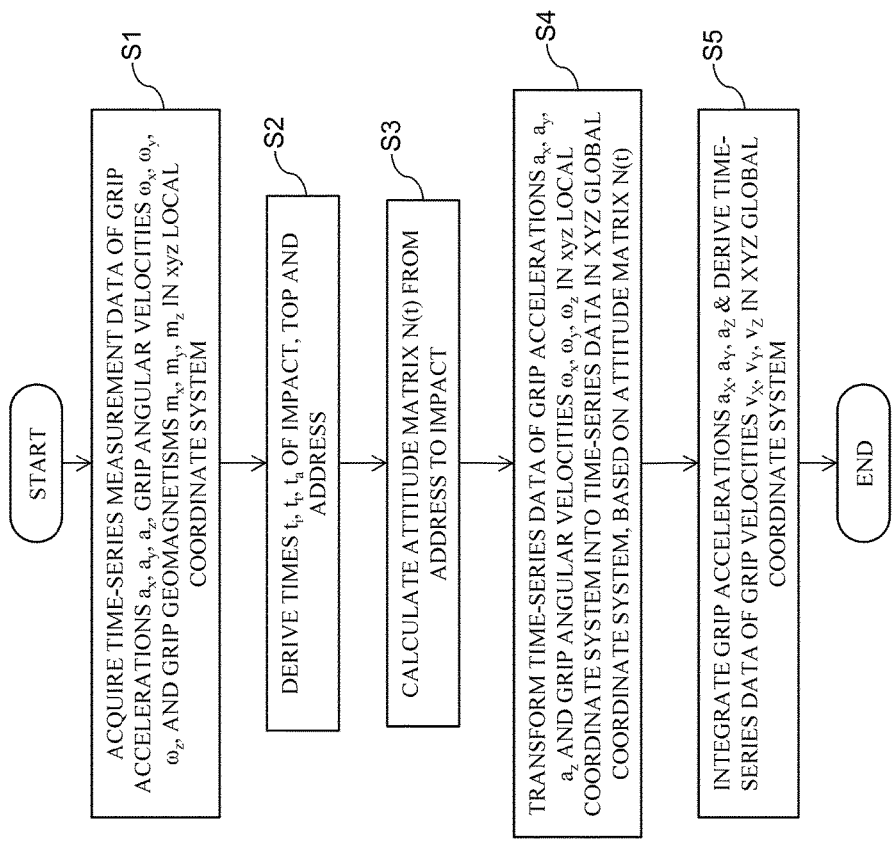
FIG. 5 is a flowchart showing the flow of a first transformation process.

Hereinafter, the first transformation process of transforming the measurement data of the xyz local coordinate system into values of the XYZ global coordinate system will be described, with reference to FIG. 5. Specifically, first, the acquisition unit 24A reads out the time-series measurement data of grip accelerations $a_x$, $a_y$, and $a_z$, grip angular velocities $\omega_x$, $\omega_y$, and $\omega_z$, and grip geomagnetisms $m_x$, $m_y$, and $m_z$ in the xyz local coordinate system that are stored in the storage unit 23 (step S1).

Next, based on the time-series measurement data of the xyz local coordinate system read at step S1, the grip behavior derivation unit 24B derives times $t_i$, $t_t$ and $t_a$ of the impact, top and address (step S2). In the present embodiment, impact time $t_i$ is derived first, top time $t_t$ is derived based on impact time $t_i$, and address time $t_a$ is derived based on top time $t_t$.

Specifically, the time at which an increment per sampling period $\Delta t$ of grip angular velocity $\omega_x$ first exceeds a threshold of 300 deg/s is set as a provisional time of impact. The time at which the increment per sampling period $\Delta t$ of grip angular velocity $\omega_x$ exceeded 200 deg/s during a period until this provisional time of impact from a predetermined amount of time before the provisional time of impact is detected and set as impact time $t_i$.

Figure 6:
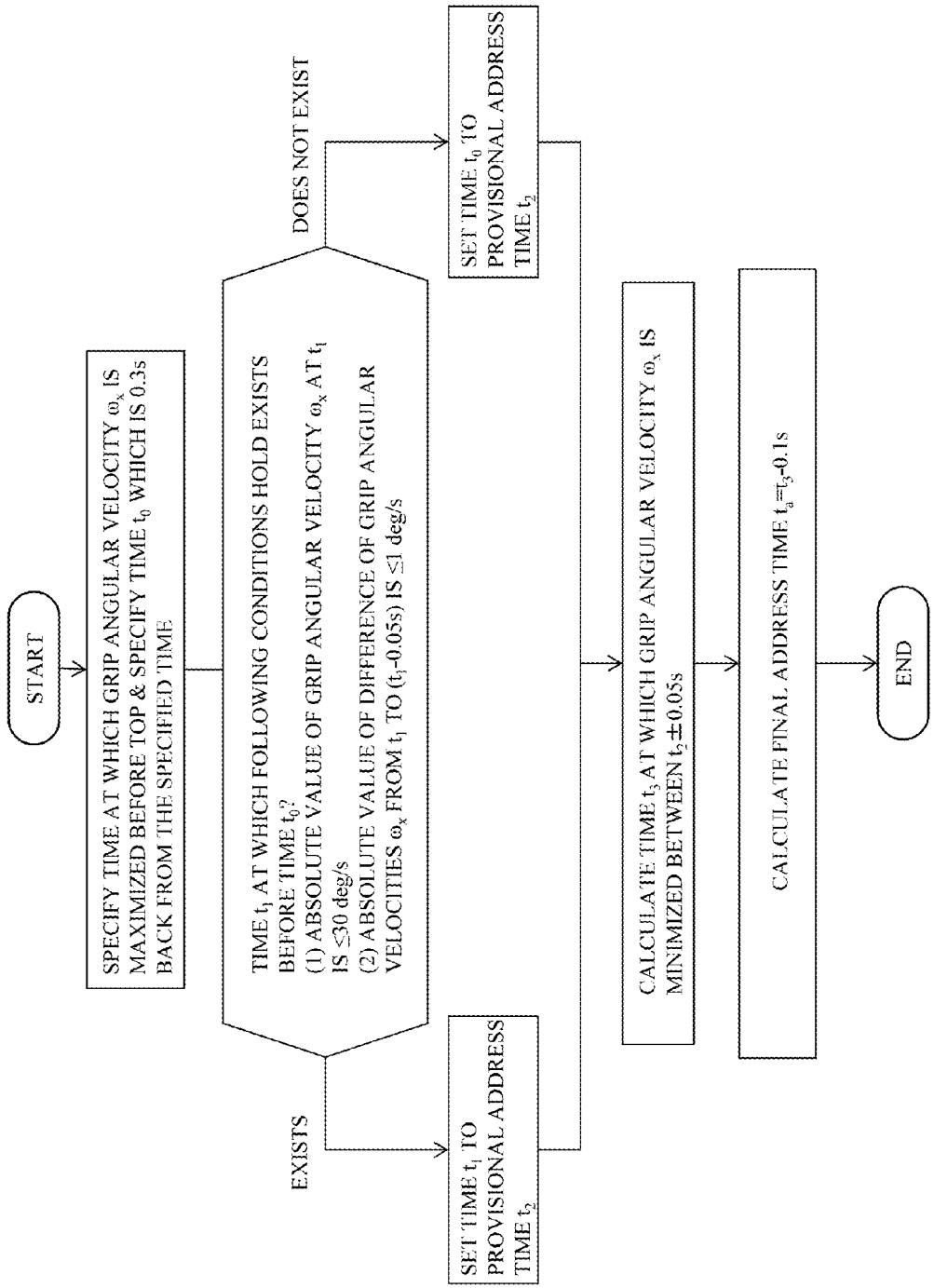
FIG. 6 is a flowchart showing the flow of processing for deriving the time of address.

Next, a time before impact time $t_i$ at which grip angular velocity $\omega_y$ changes from negative to positive is specified as top time $t_t$. Also, address time $t_a$ is calculated in accordance with the flowchart of FIG. 6.

In the following step S3, the grip behavior derivation unit 24B calculates attitude matrix N(t) at time t from address to impact. Here, assume that the attitude matrix is represented by the following equation. Attitude matrix N(t) is for transforming the XYZ global coordinate system at time t into the xyz local coordinate system.

$$N(t) = \begin{pmatrix} a & b & c \\ d & e & f \\ g & h & i \end{pmatrix}^T \qquad \text{Equation 1}$$

The nine components of attitude matrix N(t) are as follows:

Component a: the cosine of the angle formed by the X-axis of the global coordinate system and the x-axis of the local coordinate system Component b: the cosine of the angle formed by the Y-axis of the global coordinate system and the x-axis of the local coordinate system Component c: the cosine of the angle formed by the Z-axis of the global coordinate system and the x-axis of the local coordinate system Component d: the cosine of the angle formed by the X-axis of the global coordinate system and the y-axis of the local coordinate system Component e: the cosine of the angle formed by the Y-axis of the global coordinate system and the y-axis of the local coordinate system Component f: the cosine of the angle formed by the Z-axis of the global coordinate system and the y-axis of the local coordinate system Component g: the cosine of the angle formed by the X-axis of the global coordinate system and the z-axis of the local coordinate system Component h: the cosine of the angle formed by the Y-axis of the global coordinate system and the z-axis of the local coordinate system Component i: the cosine of the angle formed by the Z-axis of the global coordinate system and the z-axis of the local coordinate system Here, a vector (a, b, c) represents the unit vector of the x-axis direction, a vector (d, e, f) represents the unit vector of the y-axis direction, and a vector (g, h, i) represents the unit vector of the z-axis direction.

Also, attitude matrix N(t) can be represented by the following equation in accordance with the thinking of the Z-Y-Z system of Euler angles. Note that $\varphi$, $\theta$ and $\psi$ are the angles of rotation about the Z-axis, the Y-axis, and the Z-axis.

$$N(t) = \begin{bmatrix} \cos\phi\cos\theta\cos\varphi - \sin\phi\sin\varphi & -\cos\phi\cos\theta\sin\varphi - \sin\phi\cos\varphi & \cos\phi\sin\theta \\ \sin\phi\cos\theta\cos\varphi + \cos\phi\sin\varphi & -\sin\phi\cos\theta\sin\varphi + \cos\phi\cos\varphi & \sin\phi\sin\theta \\ -\sin\theta\cos\varphi & \sin\theta\sin\varphi & \cos\theta \end{bmatrix} \qquad \text{Equation 2}$$

In calculating attitude matrix N(t) from address to impact, first attitude matrix $N(t_a)$ at address time $t_a$ is calculated. Specifically, φ and θ at the time of address are calculated, in accordance with the following equations. Note that the following equations utilize the fact that, at the time of address, the golf club 4 is stationary and only gravity in the vertical direction is detected by the acceleration sensor 11. Grip accelerations $a_x$, $a_y$ and $a_z$ in the following equations are values at the time of address.

$$\phi = \tan^{-1}\left(\frac{a_y}{a_x}\right) \quad \text{Equation 3}$$

$$\theta = \tan^{-1}\left(\frac{\sqrt{a_x^2 + a_y^2}}{a_z}\right) \quad \text{Equation 4}$$

Next, ψ at the time of address is calculated in accordance with the following equation.

$$\varphi = \tan^{-1}\left(\frac{-m_{yi}}{m_{xi}}\right) \quad \text{Equation 5}$$

Note that the values of $m_{xi}$ and $m_{yi}$ in the above equation are calculated in accordance with the following equation. Also, grip geomagnetisms $m_x$, $m_y$ and $m_z$ in the following equation are values at the time of address.

$$\begin{bmatrix} m_{xi} \\ m_{yi} \\ m_{zi} \end{bmatrix} = \begin{bmatrix} \cos\theta\cos\phi & -\cos\theta\sin\phi & \sin\theta \\ \sin\phi & \cos\phi & 0 \\ -\sin\theta\cos\phi & \sin\theta\sin\phi & \cos\theta \end{bmatrix} \begin{bmatrix} m_x \\ m_y \\ m_z \end{bmatrix} \quad \text{Equation 6}$$

As described above, φ, θ and ψ at the time of address are calculated based on grip accelerations $a_x$, $a_y$ and $a_z$, and grip geomagnetisms $m_x$, $m_y$ and $m_z$ in the xyz local coordinate system. Attitude matrix $N(t_a)$ at the time of address is calculated by substituting the values of φ, θ and ψ into equation 2.

Next, attitude matrix N(t) from address to impact is calculated by updating attitude matrix $N(t_a)$ at the time of address momentarily at intervals of sampling period Δt. In specific terms, first, attitude matrix N(t) is represented by the following equation, using the four variables $q_1$, $q_2$, $q_3$ and $q_4$ ($q_4$ being the scalar part) of a quaternion.

$$N(t) = \begin{pmatrix} q_1^2 - q_2^2 - q_3^2 + q_4^2 & 2(q_3q_4 + q_1q_2) & 2(q_1q_3 - q_2q_4) \\ 2(q_1q_2 - q_3q_4) & -q_1^2 + q_2^2 - q_3^2 + q_4^2 & 2(q_1q_4 + q_2q_3) \\ 2(q_2q_4 + q_1q_3) & 2(q_2q_3 - q_1q_4) & -q_1^2 - q_2^2 + q_3^2 + q_4^2 \end{pmatrix}. \quad \text{Equation 7}$$

Accordingly, the four variables q1, q2, q3 and q4 of the quaternion can be calculated from equation 1 and equation 7, in accordance with the following equation.

$$q_4 = \pm\frac{1}{2}\sqrt{1 + a + e + i} \quad \text{Equation 8}$$
$$q_1 = (h - f)/4q_4$$
$$q_2 = (c - g)/4q_4$$
$$q_3 = (d - b)/4q_4$$

Here, the values of a to i defining attitude matrix $N(t_a)$ at the time of address are known. Therefore, first, the four variables q1, q2, q3 and q4 of the quaternion at the time of address are calculated, in accordance with the above equation.

Quaternion q' after a short amount of time has elapsed from time t is then represented by the following equation using quaternion q at time t.

$$q' = qdq \quad \text{Equation 9}$$

$$dq = \int \frac{d}{dt} q \, dt$$

Also, a first order differential equation representing the time variation of the four variables q1, q2, q3 and q4 of the quaternion is represented by the following equation.

$$\frac{d}{dt}\begin{pmatrix} q_1 \\ q_2 \\ q_3 \\ q_4 \end{pmatrix} = \begin{pmatrix} 0 & \omega_z & -\omega_y & \omega_x \\ -\omega_z & 0 & \omega_x & \omega_y \\ \omega_y & -\omega_x & 0 & \omega_z \\ -\omega_x & -\omega_y & -\omega_z & 0 \end{pmatrix}\begin{pmatrix} q_1 \\ q_2 \\ q_3 \\ q_4 \end{pmatrix} \quad \text{Equation 10}$$

The quaternion at time t can be sequentially updated to a quaternion at the following time t+Δt by using equations 9 and 10. Here, the quaternions from address to impact are calculated. Attitude matrix N(t) from address to impact is calculated by sequentially substituting the four variables q1, q2, q3 and q4 of the quaternions from address to impact into equation 7.

Next, at step S4, the grip behavior derivation unit 24B transforms the time-series data of grip accelerations $a_x$, $a_y$ and $a_z$ and grip angular velocities $\omega_x$, $\omega_y$ and $\omega_z$ in the xyz local coordinate system from address to impact into time-series data in the XYZ global coordinate system, based on attitude matrix N(t) from address to impact. Grip accelerations $a_X$, $a_Y$ and $a_Z$ and grip angular velocities $\omega_X$, $\omega_Y$ and $\omega_Z$ after transformation are calculated in accordance with the following equation.

$$(a_X a_Y a_Z)^T = [N(t)]^T (a_x a_y a_z)^T$$

$$(\omega_X \omega_Y \omega_Z)^T = [N(t)]^T (\omega_x \omega_y \omega_z)^T \quad \text{Equation 11}$$

In the following step S5, the grip behavior derivation unit 24B derives grip velocities $v_X$, $v_Y$ and $v_Z$ in the XYZ global coordinate system from address to impact, by integrating the time-series data of grip accelerations $a_X$, $a_Y$ and $a_Z$. At this time, offsetting is preferably performed so that grip velocities $v_X$, $v_Y$ and $v_Z$ from address to impact will be 0 m/s at the top. For example, the offsetting at an arbitrary time t is performed by subtracting (grip velocities $v_X$, $v_Y$ and $v_Z$ at top time $t_t$)×t/($t_t$−$t_a$) from grip velocities $v_X$, $v_Y$ and $v_Z$ at time t.

1-2-3. Second Transformation Process

Figure 7:
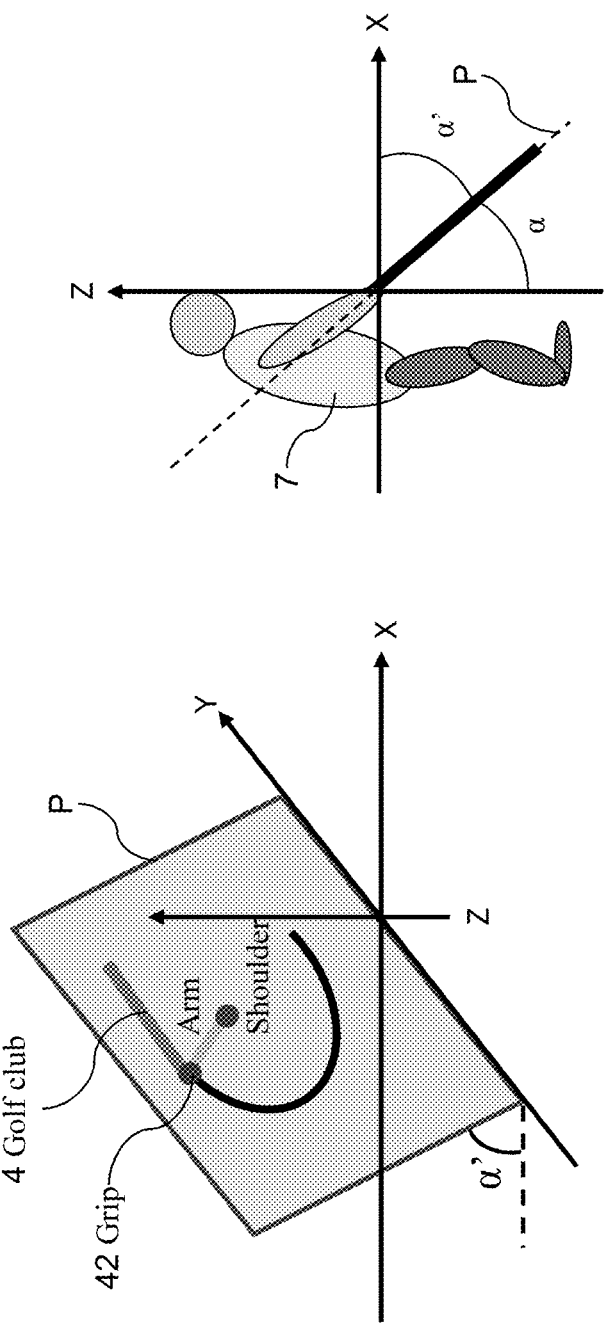
FIG. 7 is a diagram illustrating a swing plane.

Hereinafter, the second transformation process of transforming the behavior of the grip 42 in the XYZ global coordinate system calculated in the first transformation process into the behavior of the grip 42 in swing plane P will be described. In the present embodiment, swing plane P is defined as a plane that includes the origin of the XYZ global coordinate system and is parallel to the Y-axis and the shaft 40 of the golf club 4 at the time of impact (see FIG. 7). In the second transformation process, the grip behavior derivation unit 24B calculates grip velocities $v_{pX}$, $v_{pY}$ and $v_{pZ}$ and grip angular velocities $\omega_{pX}$, $\omega_{pY}$, and $\omega_{pZ}$ obtained by projecting grip velocities $v_X$, $v_Y$ and $v_Z$ and grip angular velocities $\omega_X$, $\omega_Y$ and $\omega_Z$ in the XYZ global coordinate system onto swing plane P.

Specifically, time-series data of the slope of the shaft 40 as viewed from the X-axis positive direction (the golfer 7 as viewed from the front) is calculated, based on the z-axis vector (g, h, i) that is included in attitude matrix N(t) and represents the direction in which the shaft 40 extends. The time at which the shaft 40 becomes parallel to the Z-axis as viewed from the X-axis positive direction is then specified based on this time-series data, and the specified time is set as impact time $t_i$. Note that impact time $t_i$ referred to here does not necessarily coincide with the aforementioned impact time $t_i$. Next, the slope of the shaft 40 as viewed from the Y-axis negative direction is calculated, based on the z-axis vector (g, h, i) that is included in attitude matrix N($t_i$) at this impact time $t_i$. That is, angle α' that is formed by the shaft 40 and the X-axis as viewed from Y-axis negative direction at the time of impact is calculated, and the calculated angle α' is set as the swing plane angle.

When swing plane angle α' has been derived, a projective transformation matrix A for projecting an arbitrary point in the XYZ global coordinate system onto swing plane P using the derived swing plane angle α' can be calculated as follows. Note that α=90°−α'.

$$A = \begin{bmatrix} \cos\alpha & 0 & \sin\alpha \\ 0 & 1 & 0 \\ -\sin\alpha & 0 & \cos\alpha \end{bmatrix} \quad \text{Equation 12}$$

Here, the time-series data of grip velocities $v_{pX}$, $v_{pY}$ and $v_{pZ}$ and grip angular velocities $\omega_{pX}$, $\omega_{pY}$, and $\omega_{pZ}$ after projective transformation from address to impact are calculated, in accordance with the following equation, based on the above projective transformation matrix A.

$$\begin{bmatrix} v_{pX} \\ v_{pY} \\ v_{pZ} \end{bmatrix} = \begin{bmatrix} \cos\alpha & 0 & \sin\alpha \\ 0 & 1 & 0 \\ -\sin\alpha & 0 & \cos\alpha \end{bmatrix} \quad \text{Equation 13}$$

$$\begin{bmatrix} v_X \\ v_Y \\ v_Z \end{bmatrix} = \begin{bmatrix} \cos\alpha \cdot v_X + \sin\alpha \cdot v_Z \\ v_Y \\ -\sin\alpha \cdot v_X + \cos\alpha \cdot v_Z \end{bmatrix}$$

$$\begin{bmatrix} \omega_{pX} \\ \omega_{pY} \\ \omega_{pZ} \end{bmatrix} = \begin{bmatrix} \cos\alpha & 0 & \sin\alpha \\ 0 & 1 & 0 \\ -\sin\alpha & 0 & \cos\alpha \end{bmatrix}$$

$$\begin{bmatrix} \omega_X \\ \omega_Y \\ \omega_Z \end{bmatrix} = \begin{bmatrix} \cos\alpha \cdot \omega_X + \sin\alpha \cdot \omega_Z \\ \omega_Y \\ -\sin\alpha \cdot \omega_X + \cos\alpha \cdot \omega_Z \end{bmatrix}$$

Note that the grip velocities ($v_{pY}$, $v_{pZ}$) that are obtained by the above operations represent the grip velocities (vectors) in swing plane P, and grip angular velocity $\omega_{pX}$ represents the angular velocity about the axis perpendicular to swing plane P. Here, the grip velocity (scalar) in swing plane P from address to impact is calculated in accordance with the following equation.

$$V_{GE} = \sqrt{(v_{pY})^2 + (v_{pZ})^2} \quad \text{Equation 14}$$

Also, here, the slope of the shaft 40 at the top in swing plane P, which is required in subsequent calculations, is also calculated. Specifically, first, the z-axis vector (g, h, i) that is included in attitude matrix N($t_i$) at the top is projected onto swing plane P in accordance with the following equation, using the projective transformation matrix A. Note that the vector after projection is given as (g', h', i').

$$\begin{bmatrix} g' \\ h' \\ i' \end{bmatrix} = \begin{bmatrix} \cos\alpha & 0 & \sin\alpha \\ 0 & 1 & 0 \\ -\sin\alpha & 0 & \cos\alpha \end{bmatrix} \begin{bmatrix} g \\ h \\ i \end{bmatrix} = \begin{bmatrix} \cos\alpha \cdot g + \sin\alpha \cdot i \\ h \\ -\sin\alpha \cdot g + \cos\alpha \cdot i \end{bmatrix} \quad \text{Equation 15}$$

The vector (h', i') that is specified by the above equation is a vector representing the slope of the shaft 40 at the top in swing plane P. Accordingly, the slope β of the shaft 40 at the top in swing plane P is calculated by substituting the above calculation results into the following equation.

$$\beta = \tan^{-1}\frac{i'}{h'} = \tan^{-1}\frac{-\sin\alpha \cdot g + \cos\alpha \cdot i}{h} \quad \text{Equation 16}$$

1-2-4. Shoulder Behavior Derivation Process

Figure 8:
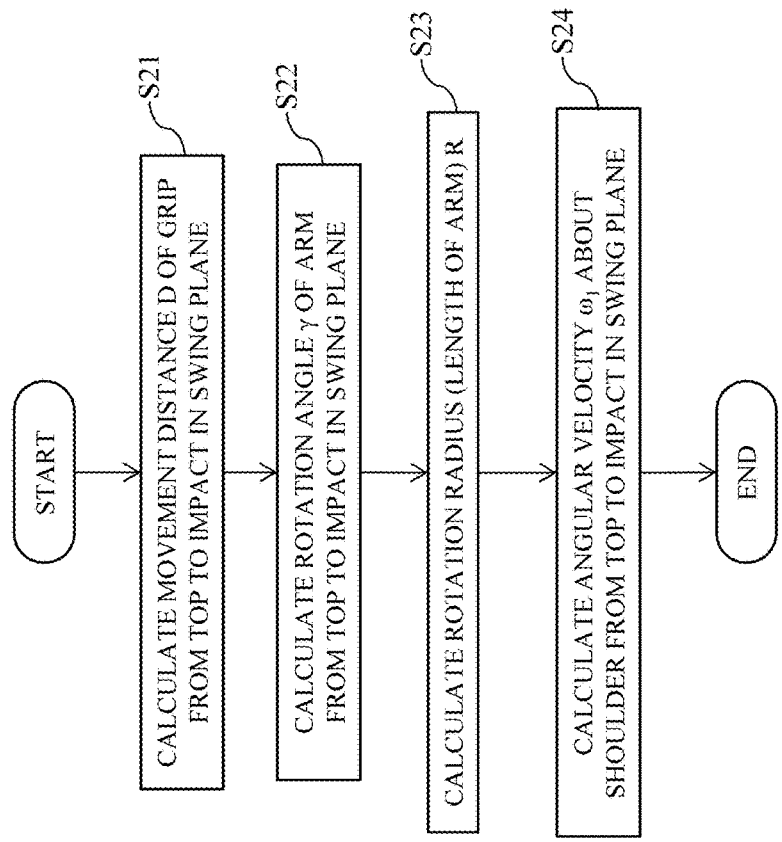
FIG. 8 is a flowchart showing the flow of a shoulder behavior derivation process.

Hereinafter, the shoulder behavior derivation process of deriving the behavior of pseudo shoulder in swing plane P based on the behavior of the grip (grip velocity $V_{GE}$ and grip angular velocity $\omega_{pX}$) in swing plane P will be described, with reference to FIG. 8. In the present embodiment, the behavior of the golf club 4 is analyzed based on a double pendulum model that takes the shoulder of the golfer 7 and the grip 42 (or the wrist of the golfer holding the grip 42) as nodes, and takes the arm of the golfer 7 and the golf club 4 as links. Note that the behavior of the shoulder is derived as the behavior of pseudo shoulder, based on the measured behavior of the grip, rather than by directly measuring the behavior of the shoulder. Hereinafter, unless stated otherwise, any reference to merely the "shoulder" is assumed to mean the pseudo shoulder. The same applies to pseudo "arm", which are defined as extending linearly between the pseudo shoulder and the grip 42 (wrist).

Figure 9:
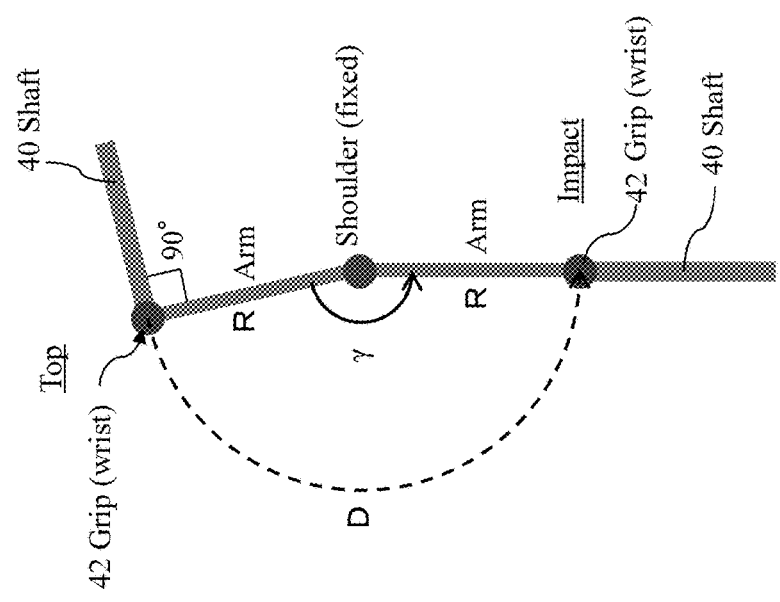
FIG. 9 is a diagram conceptually illustrating a double pendulum model.

In specifying the behavior of the shoulder from the behavior of the grip, the double pendulum model according to the present embodiment is premised on the following (1) to (5). FIG. 9 is a diagram conceptually illustrating the following preconditions.

(1) In swing plane P, the grip 42 (wrist) circulates about the shoulder.
(2) In swing plane P, a distance (radius) R between the shoulder and the grip 42 is constant.
(3) The shoulder (rotates but) does not move during the swing action.
(4) In swing plane P, the angle formed by the arm at the top and the golf club 4 is 90 degrees.
(5) The arm at the time of impact faces down in the z-axis direction as viewed from for X-axis positive direction.

Under the above premises, the shoulder behavior derivation unit 24C calculates movement distance D of the grip 42 from top to impact in swing plane P (step S21). Movement distance D is derived by integrating grip velocity $V_{GE}$ from top to impact.

Next, the shoulder behavior derivation unit 24C calculates rotation angle γ of the arm from top to impact in swing plane P (step S22). Rotation angle γ is calculated based on the slope β of the shaft 40 at the top calculated in the second transformation process. Next, the shoulder behavior derivation unit 24C calculates radius R=D/γ (step S23).

The shoulder behavior derivation unit 24C then calculates the angular velocity (angular velocity of the arm) $\omega_1$ about the shoulder from top to impact in swing plane P as the behavior of the shoulder, in accordance with the following equation (step S24). That is, angular velocity $\omega_1$ of the arm will be a value that reflects the measured grip velocity $V_{GE}$.

$$\omega_1 = V_{GE}/R$$

1-2-5. Index Calculation Process

Figure 10:
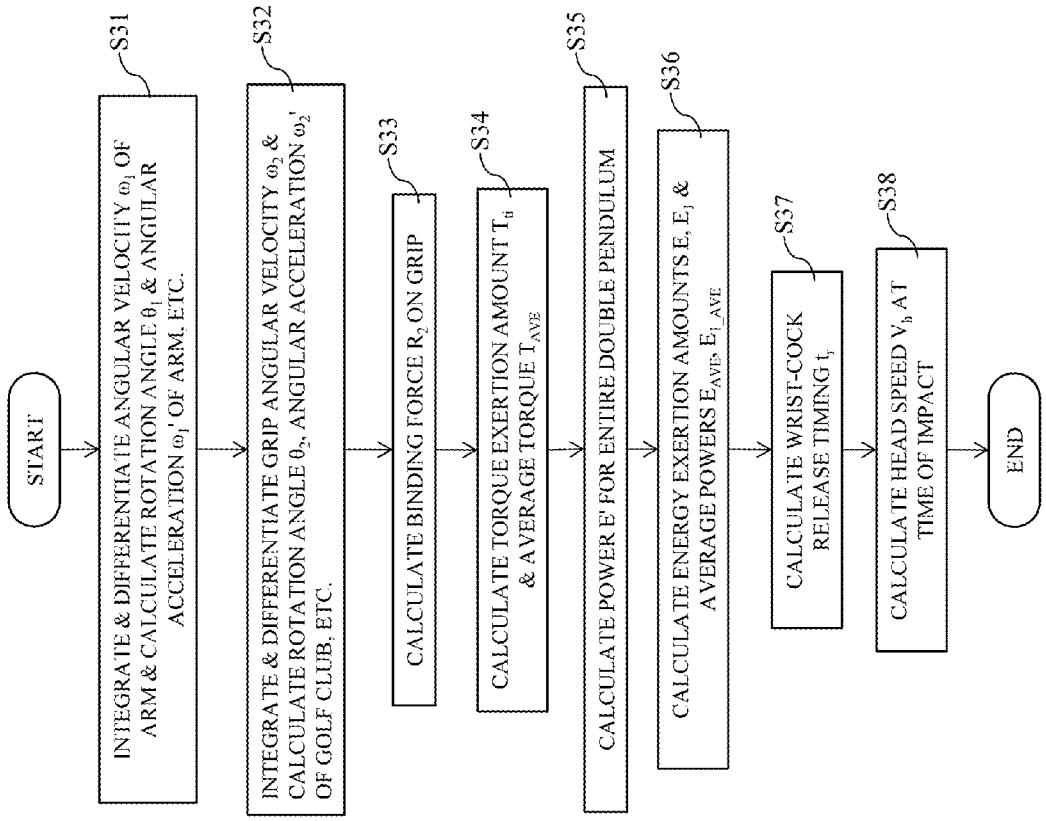
FIG. 10 is a flowchart showing the flow of an index calculation process.

Hereinafter, the index calculation process of calculating the swing index based on the behavior of the grip 42 and the behavior of the shoulder will be described, with reference to FIG. 10. In the present embodiment, torque exertion amount $T_{ti}$, average torque $T_{AVE}$, energy exertion amounts E and $E_1$, average powers $E_{AVE}$ and $E_{1\_AVE}$ and a head speed $V_h$ which will be discussed later are calculated as swing indices.

Figure 11:
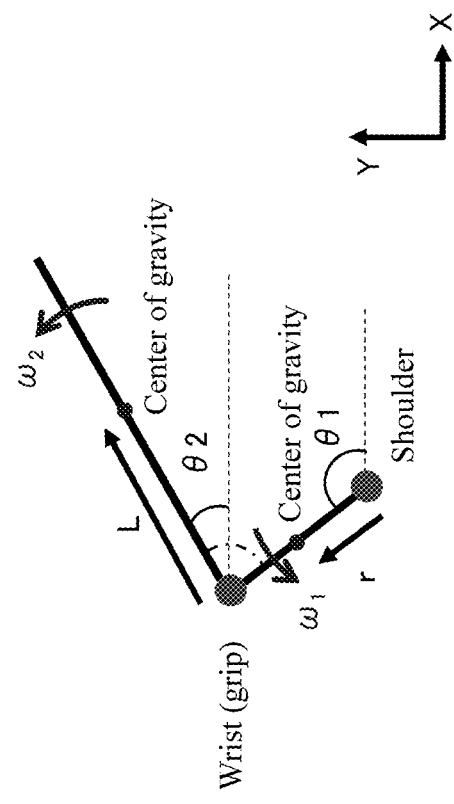
FIG. 11 is another diagram conceptually illustrating a double pendulum model.

Specifically, first, at step S31, the shoulder behavior derivation unit 24C integrates angular velocity $\omega_1$ of the arm from top to impact, calculates rotation angles $\theta_1$ of the arm from top to impact. At this time, trapezoidal integration is preferably used. Note that rotation angle $\theta_1$ is defined as shown in FIG. 11, and the plane of FIG. 11 is equal to swing plane P. Hereinafter, analysis proceeds based on the new XY coordinate system in swing plane P shown in FIG. 11. The X-axis and the Y-axis of the new XY coordinate system in swing plane P are different axes to the X-axis and the Y-axis of the abovementioned XYZ global coordinate system.

Also, the shoulder behavior derivation unit 24C differentiates angular velocity $\omega_1$ of the arm from top to impact, and calculates the angular acceleration $\omega_1'$ from top to impact. Next, the shoulder behavior derivation unit 24C calculates the position ($X_1$, $Y_1$), the velocity ($V_{X1}$, $V_{Y1}$) and the acceleration ($A_{X1}$, $A_{Y1}$) of the center of gravity of the arm from top to impact. These values are calculated by substituting the above mentioned calculation results into the following equation.

$$X_1 = r\cos\theta_1$$
$$Y_1 = r\sin\theta_1$$
$$V_{X1} = -r\omega_1 \sin\theta_1$$
$$V_{Y1} = r\omega_1 \cos\theta_1$$
$$A_{X1} = -r\omega_1' \sin\theta_1 - r\omega_1^2 \cos\theta_1$$
$$A_{Y1} = r\omega_1' \cos\theta_1 - r\omega_1^2 \sin\theta_1 \quad \text{Equation 17}$$

Note that r is the distance from the shoulder to the center of gravity of the arm. In the present embodiment, the center of gravity of the arm is assumed to be in the center of the arm. Accordingly, R=2r.

Next, at step S32, the grip behavior derivation unit 24B also performs a similar operation to step S31 with respect to the area around the grip 42. That is, angular velocity $\omega_2$ of the golf club 4 about the grip 42 from top to impact (= grip angular velocity $\omega_{pX}$ from top to impact) are integrated, and a rotation angle $\theta_2$ of the golf club 4 (shaft 40) about the grip 42 from top to impact is calculated. Trapezoidal integration is also preferably used at this time, and the rotation angle $\theta_2$ is defined as shown in FIG. 11.

Next, the grip behavior derivation unit 24B differentiates angular velocity $\omega_2$ of the golf club 4 from top to impact, and calculates angular acceleration $\omega_2'$ from top to impact. Next, the grip behavior derivation unit 24B calculates the position ($X_2$, $Y_2$), the speed ($V_{X2}$, $V_{Y2}$) and the acceleration ($A_{X2}$, $A_{Y2}$) of the center of gravity of the golf club 4 from top to impact. These values are calculated by substituting the abovementioned calculation results into the following equation.

$$X_2 = 2X_1 + L\cos\theta_2$$
$$Y_2 = 2Y_1 + L\sin\theta_2$$
$$V_{X2} = 2V_{X1} - L\omega_2 \sin\theta_2$$
$$V_{Y2} = 2V_{Y1} + L\omega_2 \cos\theta_2$$
$$A_{X2} = 2A_{X1} - L\omega_2' \sin\theta_2 - L\omega_2^2 \cos\theta_2$$
$$A_{Y2} = 2A_{Y1} + L\omega_2' \cos\theta_2 - L\omega_2^2 \sin\theta_2 \quad \text{Equation 18}$$

Note that L is the distance from the grip 42 to the center of gravity of the golf club 4. The value of L is a specification of the golf club 4, and is assumed to be determined in advance.

Next, in step S33, the index calculation unit 24D calculates binding force $R_2$ on the grip 42 from top to impact= ($R_{X2}$, $R_{Y2}$), by substituting the abovementioned calculation results into the following equation. The following equation is based on balancing translational forces. Note that $m_2$ is the mass of the golf club, and g is the gravitational acceleration. Also, $m_2$ is a specification of the golf club 4, and is assumed to be determined in advance.

$$R_{X2} = -m_2 A_{X2}$$
$$R_{Y2} = -m_2 A_{Y2} - m_2 g \sin\alpha \quad \text{Equation 19}$$

In the following step S34, the index calculation unit 24D calculates torque $T_1$ about the shoulder and torque $T_2$ about the grip 42 from top to impact, by substituting the abovementioned calculation results into the following equations.

$$T_1 = I_1\omega_1' + 2r\sin\theta_1 \cdot R_{X2} - 2r\cos\theta_1 \cdot R_{Y2} + m_1 r\cos\theta_1 \cdot A_{Y1} - m_1 r\sin\theta_1 \cdot A_{X1} + m_1 r\cos\theta_1 \cdot g\sin\alpha + T_2 \quad \text{Equation 20}$$

$$T_2 = I_2\omega_2' + m_2 L\cos\theta_2 \cdot A_{Y2} - m_2 L\sin\theta_2 \cdot A_{X2} + m_2 L\cos\theta_2 \cdot g\sin\alpha \quad \text{Equation 21}$$

Note that $I_1$ is the moment of inertia about the center of gravity of the arm, and $I_2$ is the moment of inertia about the center of gravity of the golf club 4. In the present embodiment, moment of inertia $I_1$ about the center of gravity of the arm is calculated as $I_1 = m_1 r^2/3$, assuming the center of gravity of the arm is in the center of the arm. $m_1$ is the mass of the arm, and, in the present embodiment, the mass $m_1$ of the arm is assumed to be determined in advance as appropriate. For example, before starting analysis, the weight of the golfer 7 is input, and the mass of the arm is automatically calculated by an operation such as multiplying the input weight by a predetermined coefficient. Also, $I_2$ is a specification of the golf club 4, and is assumed to be determined in advance.

In the present embodiment, the index calculation unit 24D calculates value $T_{ti}$ obtained by integrating torque $T_1$ about the shoulder for the segment from top to impact. $T_{ti}$ refers to a torque exertion amount that is exerted for the entire double pendulum from top to impact. Torque exertion amount $T_{ti}$ is one of the swing indices. Also, the index calculation unit 24D calculates $T_{AVE}=T_{ti}/(t_i-t_t)$, which is the average torque per unit time (average torque) that is exerted for the entire double pendulum from top to impact. The average torque $T_{AVE}$ is also a swing index. Note that in calculating torque exertion amount $T_{ti}$, a configuration may be adopted in which only positive torque $T_1$ is integrated or in which the average value of torque $T_1$ is integrated.

In the following step S35, the index calculation unit 24D calculates power E' for the entire double pendulum from top to impact based on the abovementioned calculation results. The power E' for the entire double pendulum is calculated as the sum of power $E_1$' of the arm and power $E_2$' of the golf club 4. Specifically, E' is represented in accordance with the following equation, where $v_s$ is the velocity vector of the shoulder and $v_g$ is the velocity vector of the grip 42. Note that $R_1$ is the binding force on the shoulder. Also, $v_s$ and $v_g$ can respectively be calculated through first order differentiation such that position vector $d_s$ of the shoulder and position vector $d_g$ of the grip 42=$d_s$+(2$X_1$, 2$Y_1$).

$$E_1'=-R_1v_s^T+R_2v_g^T+T_1\omega_1-T_2\omega_1$$

$$E_2'=-R_2v_g^T+T_2\omega_2$$

$$E'=E_1'+E_2'=-R_1v_s^T+T_1\omega_1+T_2(\omega_2-\omega_1) \quad \text{Equation 22}$$

Also, in the present embodiment, $v_s$=(0, 0) since the shoulder does not move, and power E' for the entire double pendulum is calculated in accordance with the following equation. The index calculation unit 24D calculates power E' for the entire double pendulum from top to impact by substituting the abovementioned calculation results into the following equation.

$$E_1'=R_2v_g^T+T_1\omega_1-T_2\omega_1$$

$$E_2'=-R_2v_g^T+T_2\omega_2$$

$$E'=T_1\omega_1+T_2(\omega_2-\omega_1) \quad \text{Equation 23}$$

Figure 12:
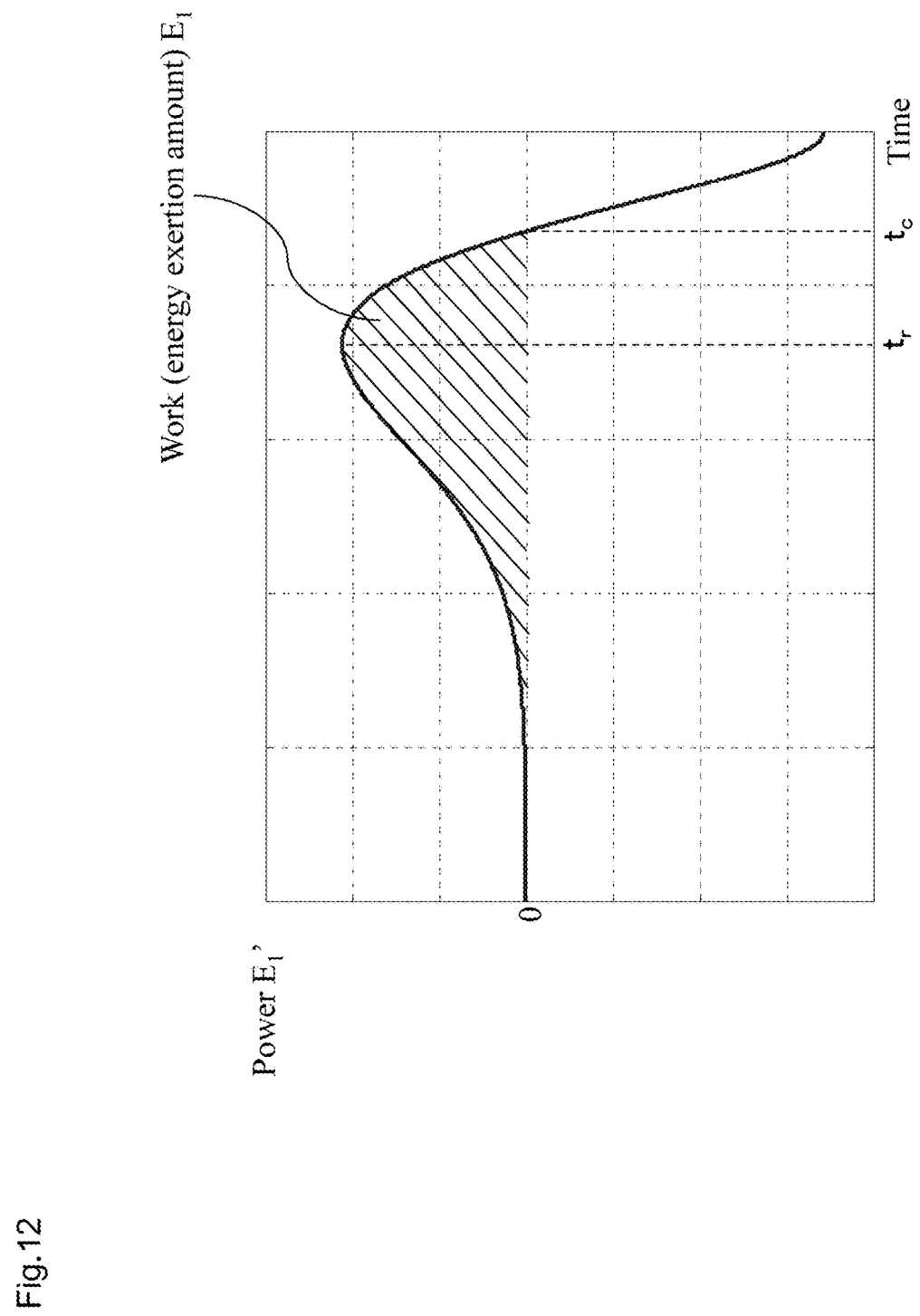
FIG. 12 is a diagram illustrating an energy exertion amount which is one swing index.

In the following step S36, the index calculation unit 24D specifies time $t_c$ at which power $E_1$' of the arm changes from positive to negative after the top, and calculates work (energy) $E_1$ of the arm from time $t_t$ to time $t_c$. Work $E_1$ of the arm is calculated by integrating power $E_1$' of the arm for the segment from time $t_t$ to time $t_c$ (see FIG. 12). Note that work $E_1$ can be taken as an index representing the work (energy) that is exerted by the arm between times $t_t$ and $t_c$, and thus, in this sense, can be called the energy exertion amount of the arm. Also, the index calculation unit 24D calculates $E_{1\_AVE}$=$E_1/(t_c-t_t)$, based on energy exertion amount $E_1$. $E_{1\_AVE}$ refers to the average power of the arm between times $t_t$ and $t_c$, or the amount of energy per average unit of time (average energy exertion amount) that is exerted by the arm between times $t_t$ and $t_c$. Energy exertion amount $E_1$ and average power (average energy exertion amount) $E_{1\_AVE}$ are both swing indices.

Also, the index calculation unit 24D specifies time $t_d$ at which power E' for the entire double pendulum changes from positive to negative after the top, and calculates work (energy) E for the entire double pendulum from time $t_t$ of the top to time $t_d$. Work E for the entire double pendulum is calculated by integrating power E for the entire double pendulum for the segment from time $t_t$ to time $t_d$. Note that work E can be taken as an index representing the work (energy) for the entire double pendulum from time $t_t$ to time $t_d$, and thus, in this sense, can be called the energy exertion amount for the entire double pendulum. Also, the index calculation unit 24D calculates $E_{AVE}$=E/($t_d-t_t$) based on energy exertion amount E. $E_{AVE}$ refers to the average power for the entire double pendulum between times $t_t$ and $t_d$, or to the amount of energy per average unit of time (average energy exertion amount) that is exerted for the entire double pendulum between times $t_t$ and $t_d$. Energy exertion amount E and average power (average energy exertion amount) $E_{AVE}$ are both swing indices.

In the following step S37, the index calculation unit 24D calculates wrist-cock release timing $t_r$ that occurs during the swing. Note that the inventors found, through testing, that head speed $V_h$ at the time of the impact, which is a swing index, is correlated with each of wrist-cock release timing $t_r$ during the swing, energy exertion amount $E_1$, and average power (average energy exertion amount) $E_{1\_AVE}$. In view of this, here, wrist-cock release timing $t_r$ is calculated in order to calculate head speed $V_h$ at the time of impact. In the present embodiment, with regard to the wrist-cock release timing, the time at which power $E_1$' is maximized in the segment from time $t_t$ to time $t_c$ (or $t_t$ to $t_d$) is specified as wrist-cock release timing $t_r$ (see FIG. 12).

In the following step S38, the index calculation unit 24D calculates head speed $V_h$ at the time of impact, based on wrist-cock release timing $t_r$ and average power $E_{1\_AVE}$. Specifically, head speed $V_h$ at the time of impact is calculated according to the following equation. Note that $k_1$, $k_2$ and $k_3$ are constants obtained from the results of a large number tests carried out in advance by multiple regression analysis, and are held in advance in the storage unit 23. This ends the index calculation process.

$$V_h=k_1\cdot E_{1\_AVE}+k_2\cdot t_r+k_3$$

1-2-6. Output Process

When the index calculation process has ended, the display control unit 24E displays the calculated swing index (torque exertion amount $T_{ti}$, average torque $T_{AVE}$, energy exertion amounts E, $E_1$, average powers $E_{AVE}$, $E_{1\_AVE}$, and head speed $V_h$) on the display unit 21. The user can thereby comprehend the swing indices corresponding to the golf club 4 that was swung, and can judge whether the golf club 4 is suited to the golfer 7.

Note that although the flow of processing by which swing indices are calculated based on one swing action has been described above, the golfer 7 can take practice hits with various golf clubs 4, and swing indices for the various golf clubs 4 can be repeatedly calculated. In this case, the display control unit 24E collates these swing indices into the form of tables, graphs or the like that are then displayed on the display unit 21. Note that, for example, the tables and/or graphs at this time are able to show the correspondence relationship of the swing indices with the number and/or specifications of the golf club 4 with which the practice hits were taken. Also, specifications include the weight, loft angle and shaft length of the golf club, for example. The user is thereby able to easily select a golf club 4 providing optimal swing indices from among a variety of golf clubs 4.

2. Second Embodiment 2-1. Schematic Configuration of Golf Club Fitting System

Figure 14:
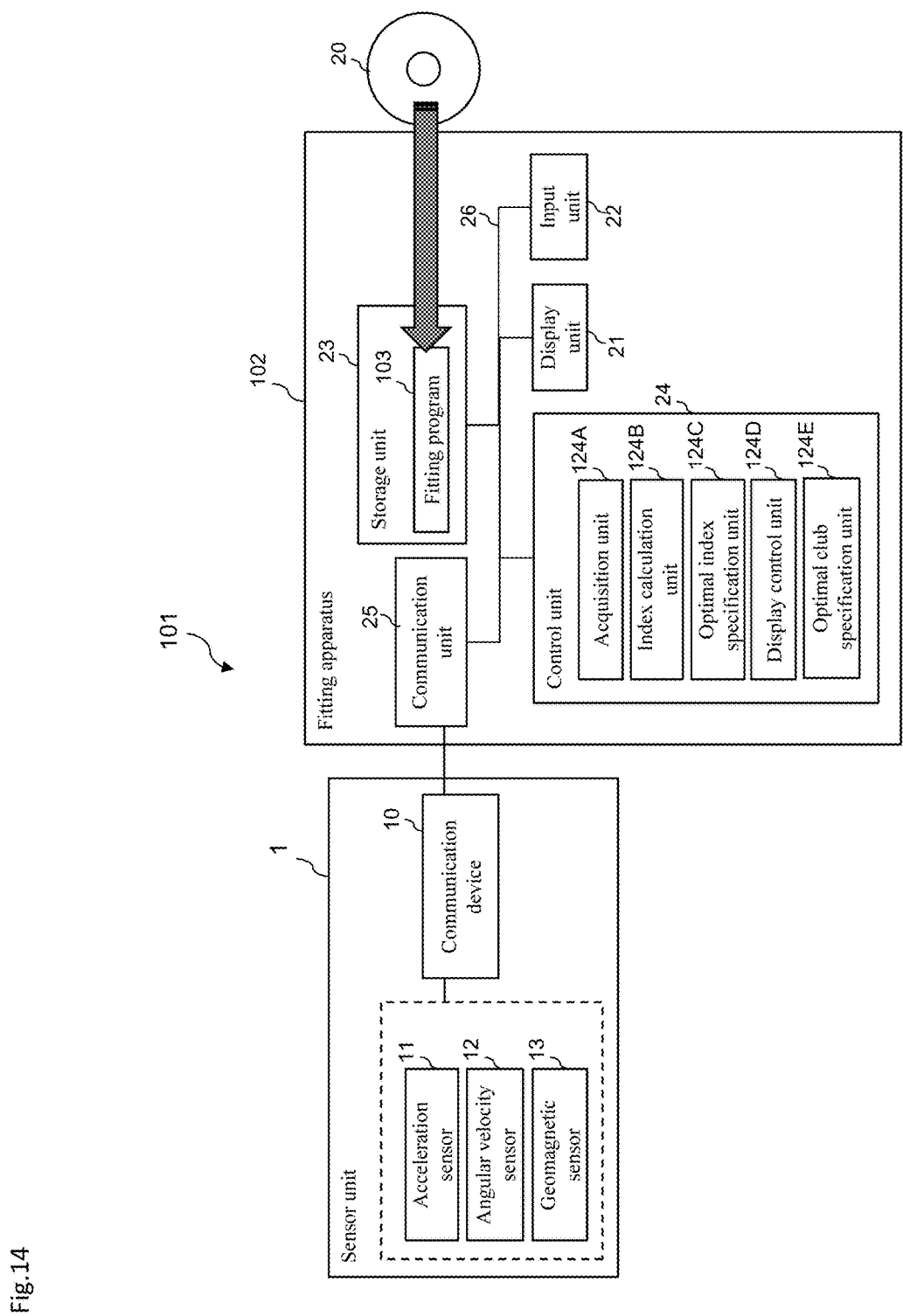
FIG. 14 is a functional block diagram of a golf swing analysis system according to a second embodiment of the present invention.

Hereinafter, a fitting system (hereinafter, analysis system 101) that is provided with a fitting apparatus 102 for fitting the golf club 4 according to the second embodiment will be described. The analysis system 101 referred to here has many points in common with the analysis system 100 according to the first embodiment. Hereinafter, for ease of understanding, the description will focus on the differences between the embodiments, with the same reference numerals being given to constituent elements that are same, and description thereof being omitted. FIG. 14 shows the overall configuration of an analysis system 101 according to the present embodiment. The fitting apparatus 102 assists selection of a golf club 4 suited to the golfer 7, based on measurement data obtained by measuring the swing action of the golf club 4 by the golfer 7. The swing action is measured by the sensor unit 1 (measurement device) attached to the grip 42 of the golf club 4. The fitting apparatus 102 constitutes the analysis system 101 together with this sensor unit 1.

Hereinafter, the configuration of the fitting apparatus 102 will be described, followed by description of the flow of fitting processing. With regard to the configuration of the sensor unit 1, the description in 1-1-1 above applies to the second embodiment simply by reading the fitting apparatus 102 in place of the analysis apparatus 2, and thus detailed description thereof will be omitted here.

The configuration of the fitting apparatus 102 will be described with reference to FIG. 14. The fitting apparatus 102 is manufactured by installing a golf club fitting program 103 according to the present embodiment that is stored in a computer readable recording medium 20 such as a CD-ROM or a USB memory on a general-purpose personal computer from the recording medium 20. The fitting program 103 is software for analyzing a swing action based on measurement data sent from the sensor unit 1, and outputting information that assists selection of a golf club suited to the golfer 7. The fitting program 103 causes the fitting apparatus 102 to execute operations which will be discussed later.

The hardware configuration of the fitting apparatus 102 is similar to the analysis apparatus 2 according to the first embodiment. In the fitting apparatus 102, however, the fitting program 103 is installed instead of the analysis program 3. Thus, the control unit 24 operates in a virtual manner as an acquisition unit 124A, an index calculation unit 124B, an optimal index specification unit 124C, a display control unit 124D, and an optimal club specification unit 124E, by reading and executing the fitting program 103 stored in the storage unit 23. The operations of each of the units 124A to 124E will be discussed in detail later.

2-2. Fitting Processing

Next, the flow of processing for fitting a golf club 4 by the analysis system 101 will be described. The fitting processing according to the present embodiment is constituted by the following seven processes.

(1) A measurement process of measuring measurement data of grip accelerations $a_x$, $a_y$ and $a_z$, grip angular velocities $\omega_x$, $\omega_y$, and $\omega_z$, and grip geomagnetisms $m_x$, $m_y$ and $m_z$ in the xyz local coordinate system.

(2) A first transformation process of transforming the measurement data of the xyz local coordinate system that was acquired in the measurement process into grip accelerations $a_X$, $a_Y$ and $a_Z$ and grip angular velocities $\omega_X$, $\omega_Y$, and $\omega_Z$ in the XYZ global coordinate system (in the first transformation process, grip velocities $v_X$, $v_Y$ and $v_Z$ in the XYZ global coordinate system are also derived).

(3) A second transformation process of transforming the behavior (grip angular velocities $\omega_X$, $\omega_Y$ and $\omega_Z$ and grip velocities $v_X$, $v_Y$ and $V_Z$) of the grip 42 in the XYZ global coordinate system into the behavior of the grip 42 in swing plane P (discussed later).

(4) A shoulder behavior derivation process of deriving the behavior of pseudo shoulder of the golfer 7 in swing plane P, based on the behavior of the grip 42 in swing plane P.

(5) An index calculation process of calculating a swing index (in the present embodiment, head speed) that characterizes the swing action, based on the behavior of the grip 42 and the behavior of the pseudo shoulder.

(6) An optimal index specification process of plotting the values of the swing index calculated in the index calculation process in a swingability index-swing index plane, and specifying an optimal swingability index for the golfer 7 (in the present embodiment, weight of the golf club 4).

(7) An optimal club specification process of specifying a golf club that can particularly increase head speed, from among a plurality of golf clubs that match the optimal swingability index specified in the optimal index specification process.

Hereinafter, these processes will be described in the above order.

2-2-1. Measurement Process

In the measurement process, the golfer 7 swings a plurality of golf clubs 4 having the sensor unit 1. In the present embodiment, practice hits are taken with one extremely light golf club 4 and two extremely heavy golf clubs. At this time, the difference in weight between the extremely light golf club 4 and the extremely heavy golf clubs 4 (the lighter of the two) is preferably not less than 30 g, and is more preferably not less than 40 g. Also, the difference in weight between the two extremely heavy golf clubs 4 is preferably not less than 5 g, and is more preferably not less than 10 g. For example, three golf clubs 4 having respective weights of 275 g, 315 g and 325 g can be selected.

Also, in the present embodiment, an optimal weight of the golf club 4 is calculated as an optimal swingability index for the golfer 7. Thus, the golf clubs 4 for taking practice hits with are preferably provided to suit the wishes of the golfer 7 with regard to specifications of the golf clubs 4 other than weight, such as length and balance. Furthermore, golf clubs 4 of various weights can easily be provided for taking practice hits with, by using golf clubs 4 in which various weights for weight adjustment can be inserted into a region such as the head and/or grip end of the golf club 4.

Next, measurement data of grip accelerations $a_x$, $a_y$ and $a_z$, grip angular velocities $\omega_x$, $\omega_y$ and $\omega_z$, and grip geomagnetisms $m_x$, $m_y$ and $m_z$ during swinging of a plurality of golf clubs 4 as described above is measured by the sensor unit 1. This measurement data is transmitted to the fitting apparatus 102 via the communication device 10 of the sensor unit 1. On the other hand, in the fitting apparatus 102, the acquisition unit 124A receives this measurement data via the communication unit 25, separates the received data by golf club 4, and stores the separated data in the storage unit 23. In the present embodiment, time-series measurement data at least from address to impact is measured.

Also, in the measurement process, multiple practice hits are preferably taken with each of the above plurality of golf clubs 4, with five practice hits or more being preferable. In this case, the average value of the measurement data from one golf club 4 can be calculated and used in subsequent operations. Also, in order to remove abnormal values caused by miss hits, measurement errors or the like, it is preferable to calculate standard deviation σ of the measurement data to obtain measurement data in which the measurement data of all the practice hits preferably falls within an average value±1.65σ, and more preferably falls within an average value±1.28σ. In the case where standard deviation σ of the measurement data is calculated by the control unit 24 in order to perform this check, and the value of σ does not meet the above conditions, a message seeking additional measurement or remeasurement may then be displayed on the display unit 21. Note that a configuration may be adopted in which, rather than the average value of the measurement data itself, the average value of processing values (e.g., head speed $V_h$ discussed later) is calculated based on the measurement data. A check on the reliability of data based on standard deviation σ can also be performed in the case of calculating the average value of processing values.

2-2-2. First Transformation Process

The first transformation process is the same as the first transformation process according to the first embodiment described in the above section 1-2-2. That is, since the description relating to the first transformation process described in section 1-2-2 is also applicable to the second embodiment simply by reading the index calculation unit 124B in place of the grip behavior derivation unit 24B, a detailed description will be omitted here. Note that, in section 1-2-2, processing based on measurement data from one golf club 4 was described for the sake of simplicity, although, in actuality, similar processing is performed on the measurement data of each golf club 4. The same applies to the subsequent second transformation process, shoulder behavior derivation process, and index calculation process.

2-2-3. Second Transformation Process

The second transformation process is also similar to the first embodiment. That is, since the description relating to the second transformation process described in the above section 1-2-3 is also applicable to the second embodiment simply by reading the index calculation unit 124B in place of the grip behavior derivation unit 24B, a detailed description will be omitted here.

2-2-4. Shoulder Behavior Derivation Process

The shoulder behavior derivation process is also similar to the first embodiment. That is, since the description relating to the shoulder behavior derivation process described in section 1-2-4 is also applicable to the second embodiment simply by reading the index calculation unit 124B in place of the shoulder behavior derivation unit 24C, a detailed description thereof will be omitted here.

2-2-5. Index Calculation Process

Figure 15:
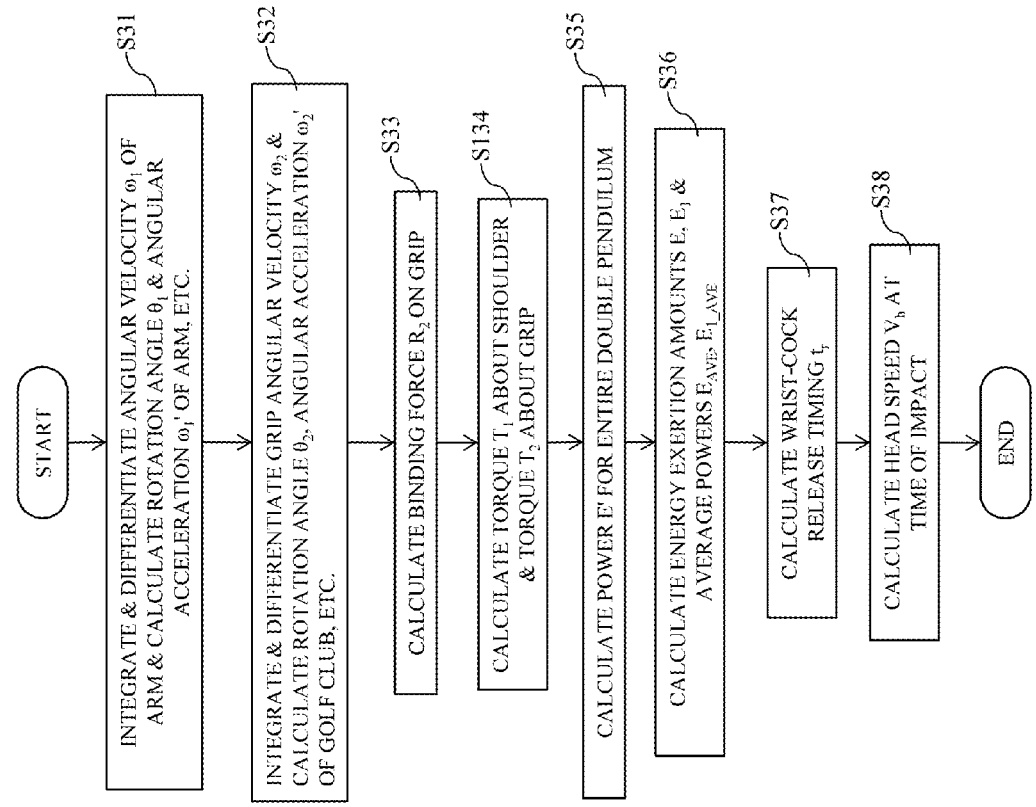
FIG. 15 is a flowchart showing the flow of an index calculation process according to the second embodiment.
Figure 16:
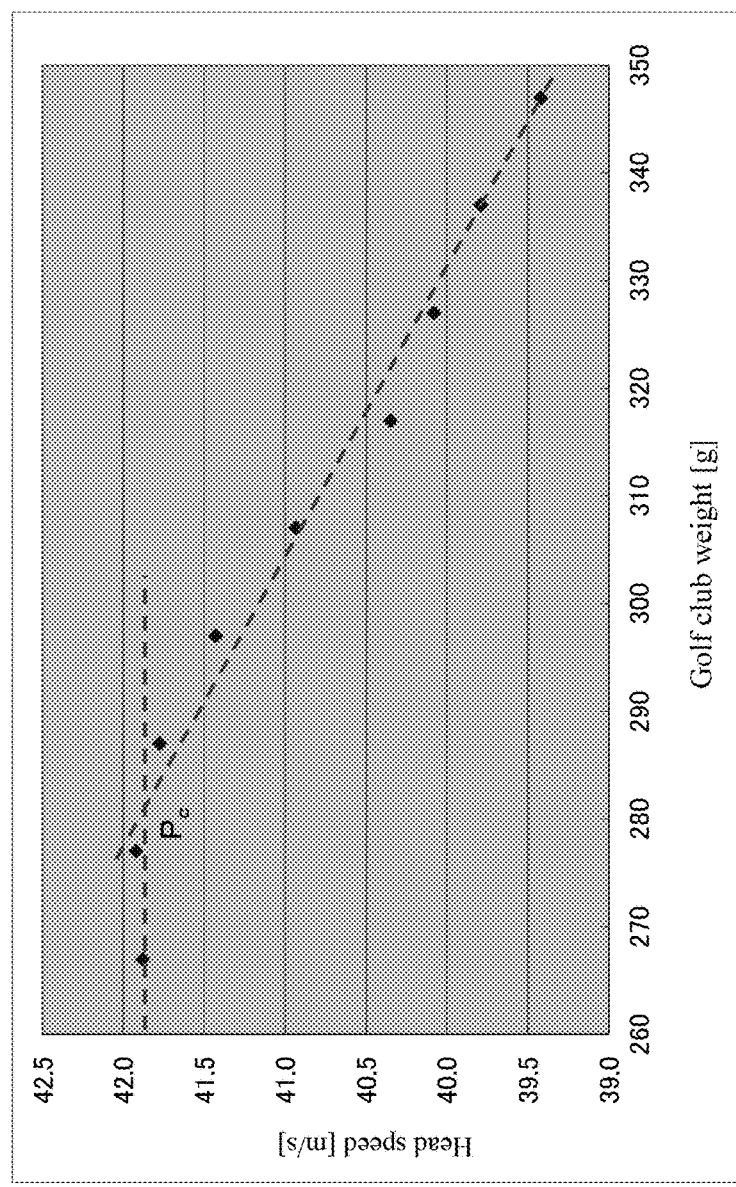
FIG. 16 shows first test data showing a relationship between head speed and golf club weight.
Figure 17:
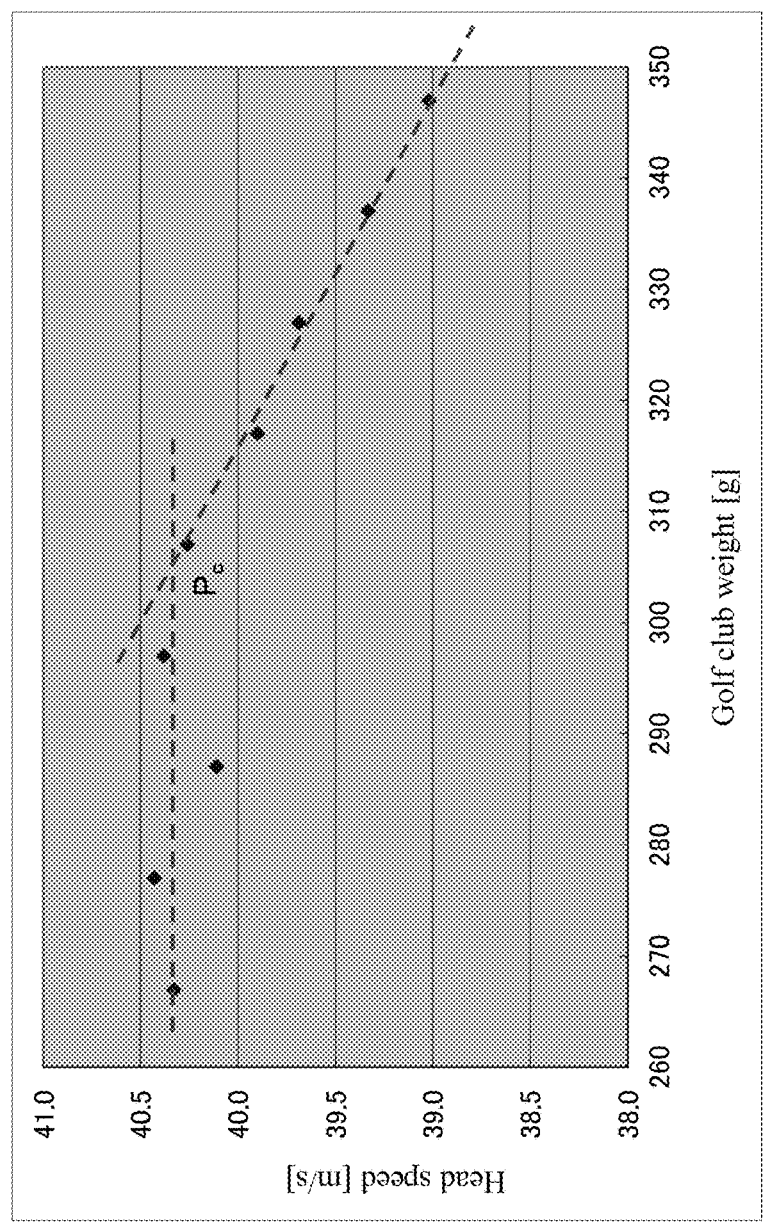
FIG. 17 shows second test data showing a relationship between head speed and golf club weight.
Figure 18:
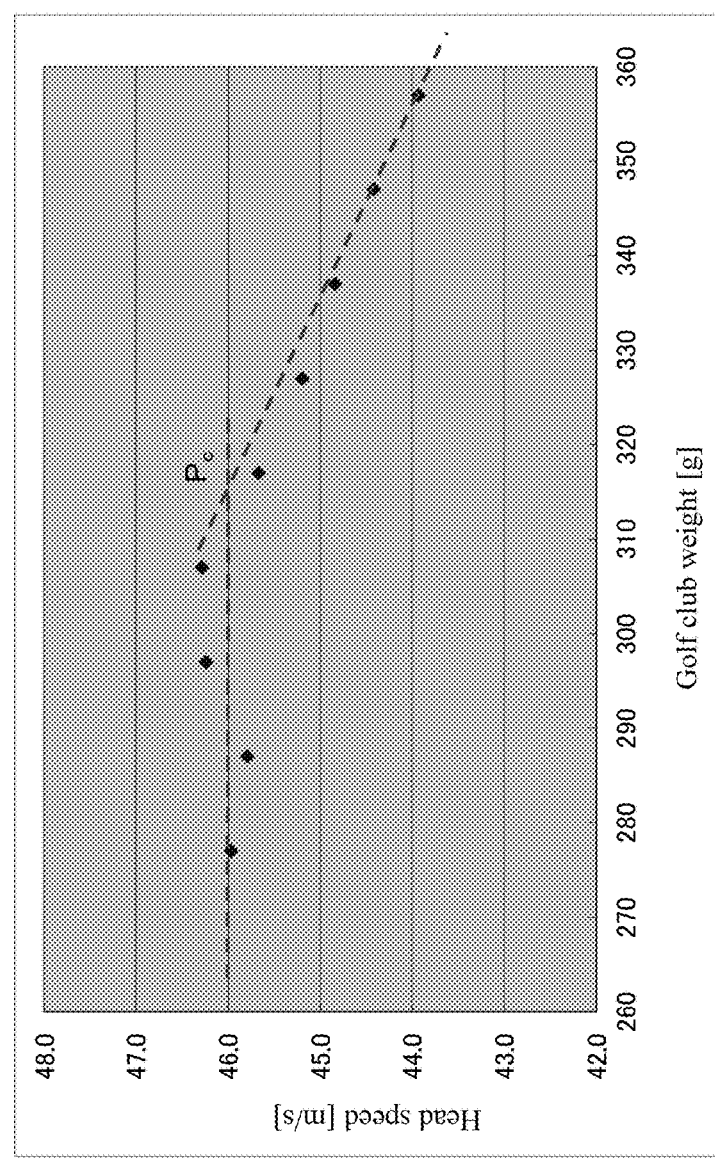
FIG. 18 shows third test data showing a relationship between head speed and golf club weight.
Figure 19:
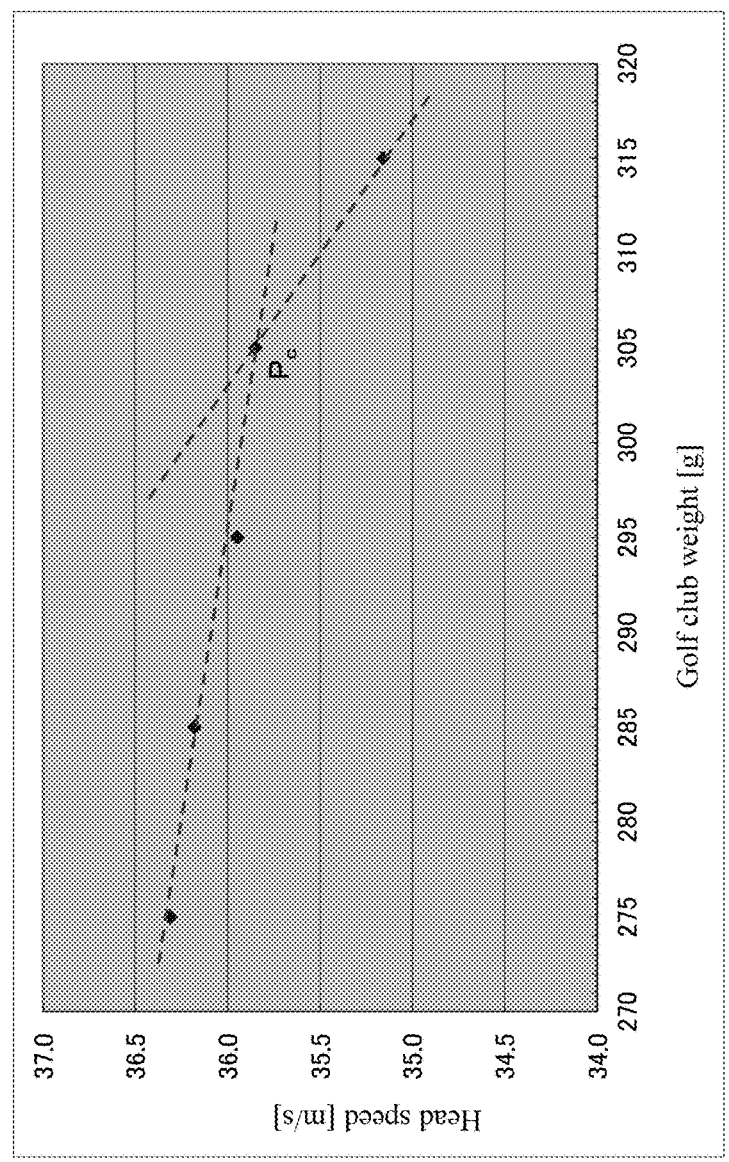
FIG. 19 shows fourth test data showing a relationship between head speed and golf club weight.

FIG. 15 shows the flow of the index calculation process according to the second embodiment. In the present embodiment, head speed $V_h$ is calculated as the swing index. The index calculation process according to the second embodiment is similar to the index calculation process according to the first embodiment, except that step S134 is executed in place of step S34. Also, step S134 is similar to step S34, except that calculation of torque exertion amount $T_h$ and average torque $T_{AVE}$ is omitted. That is, since the description relating to the index calculation process described in section 1-2-5 is also applicable to the second embodiment simply by reading the index calculation unit 124B in place of the shoulder behavior derivation unit 24C, the grip behavior derivation unit 24B and the index calculation unit 24D, a detailed description thereof will be omitted here.

When the index calculation process has ended, head speed $V_h$ deriving from the one extremely light golf club 4 and head speed $V_h$ deriving from the two extremely heavy golf clubs 4 are then calculated. Hereinafter, head speed $V_h$ deriving from the one extremely light golf club 4 is represented as $V_{h1}$, head speed $V_h$ deriving from the lighter of the two extremely heavy golf clubs 4 is represented as $V_{h2}$, and head speed $V_h$ deriving from the heavier of the two extremely heavy golf clubs 4 is represented as $V_{h3}$.

2-2-6. Optimal Index Specification Process

Hereinafter, the optimal index specification process of specifying optimal weight $m_{OP}$ of a golf club 4 suited to the golfer 7 based on head speeds $V_{h1}$ to $V_{h3}$, which are swing indices calculated in the index calculation process, will be described. Specifically, in the present embodiment, optimal weight $m_{OP}$ is specified based on a graph obtained by plotting the values of head speeds $V_{h1}$ to $V_{h3}$ in an $m_2$ (golf club weight)–$V_h$ (head speed) plane.

Figure 13A:
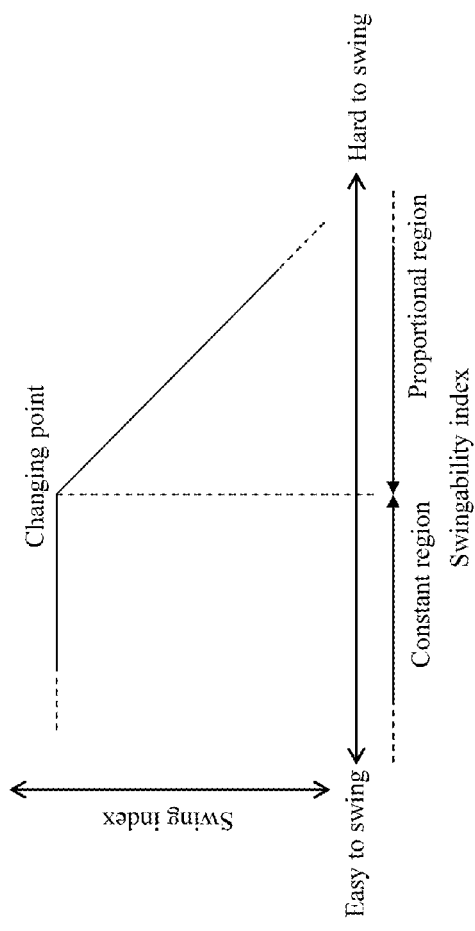
FIGS. 13A and 13B are diagrams showing a relationship between swing index and swingability index.
Figure 13B:
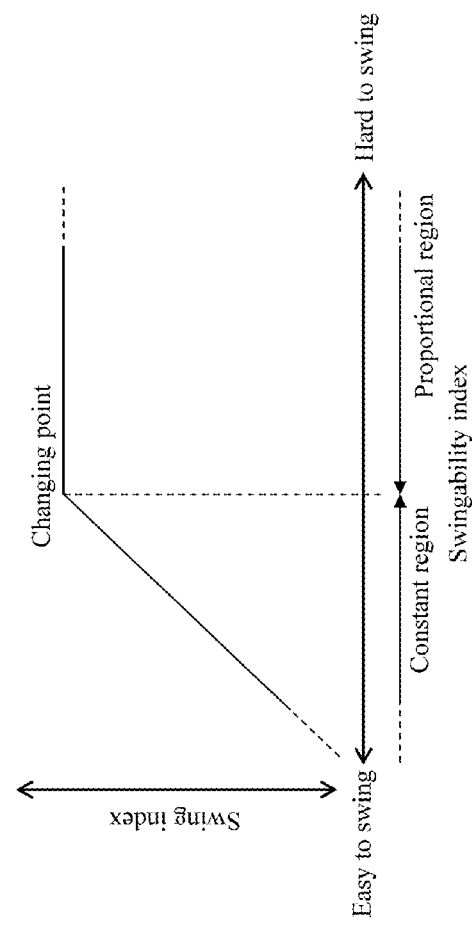

Note that an algorithm of the optimal index specification process described below is based on head speed $V_h$ and golf club weight $m_2$ having a relationship such as shown in FIGS. 13A and 13B. FIGS. 16 to 19 show examples of graphs in which measurement data obtained when four golfers take practice hits with golf clubs of various weights is plotted in the $m_2$–$V_h$ plane. It is evident from these graphs that head speed $V_h$ is divided at a certain point $P_c$ into a proportional region in which head speed $V_h$ is proportional to golf club weight $m_2$ and a constant region in which head speed $V_h$ is roughly constant regardless of golf club weight $m_2$. That is, when the golf club becomes heavier, the golfer becomes unable to freely swing the golf club and head speed $V_h$ decreases. Head speed $V_h$ plateaus after the weight of the golf club drops to a certain level, since the golf club cannot be swung at greater than the power used for a full swing. That is, it is evident that there exists a point at which the golfer's limits are reached, and head speed $V_h$ stops increasing even if the golf club becomes lighter. It is thought that, given the same head speed $V_h$, kinetic energy increases as golf club weight $m_2$ increases, leading to an increase in the initial velocity of the golf ball. Accordingly, from the viewpoint of lengthening the carry distance, a golf club weight corresponding to changing point $P_c$ can be said to be optimal.

Based on the above findings, first, the optimal index specification unit 124C plots point $P_1$ corresponding to head speed $V_{h1}$ in the $m_2$–$V_h$ plane, and specifies straight line (first regression line) that passes through point $P_1$ and has a zero slope (see FIG. 20A).

Next, the optimal index specification unit 124C plots points $P_2$ and $P_3$ corresponding to head speeds $V_{h2}$ and $V_{h3}$ in the $m_2$–$V_h$ plane, and specifies a straight line $l_2$ (second regression line) that passes through points $P_2$ and $P_3$ (see FIG. 20B).

Next, the optimal index specification unit 124C specifies intersection point $P_c$ of straight lines and $l_2$, specifies golf club weight $m_2$ corresponding to intersection point $P_c$, and takes the specified golf club weight $m_2$ as optimal weight $m_{op}$ (see FIG. 20C). Note that, in the present embodiment, it is judged whether $V_{h2} > V_{h3}$ and whether point $P_c$ lies between point $P_1$ and point $P_2$, in order to check the reliability of the measurement data. If this condition is not met, it is judged that measurement was not performed correctly, and a message seeking remeasurement is output on the display unit 21. If, in the case where point $P_c$ is on the left of point $P_1$, the correlation coefficient of the regression line of the three points $P_c$, $P_1$ and $P_2$ is greater than or equal to a predetermined value (e.g., 0.8 or greater), golf club weight $m_2$ corresponding to $P_1$ can also be taken as golf club weight $m_{op}$ without performing error processing.

The optimal index specification unit 124C then specifies a region having a predetermined width centered on optimal weight $m_{op}$, and takes the specified region as an optimal weight range of the golf club 4 (see FIG. 20D). This is for absorbing the influence of error. Specifically, the optimal weight range can be set as a region of +5 g centered on optimal weight $m_{op}$, for example. In this case, the width of the optimal weight may be reduced if the abovementioned σ is less than or equal to a predetermined value, since it is judged that accurate measurement is being performed. For example, the optimal weight range can be taken as a region of ±3 g centered on optimal weight $m_{op}$.

When the above processing has ended, the display control unit 124D displays optimal weight $m_{op}$ and the optimal weight range on the display unit 21. The golfer 7 can thereby comprehend weight $m_{op}$ of an optimal golf club 4 and an optimal weight range in the vicinity thereof for himself or herself, and can select golf clubs 4 based on this information. The display control unit 124D is also able to combine display of the graph shown in FIG. 20D on the display unit 21, in order to improve the persuasiveness of the above output values. The display control unit 124D is also able to display the calculated energy exertion amounts E and $E_1$ and average powers $E_{AVE}$ and $E_{1\_AVE}$ on the display unit 21 as references in addition to head speed $V_h$.

2-2-7. Optimal Club Specification Process

Hereinafter, the optimal club specification process of specifying a golf club (hereinafter, optimal club) that can particularly increase head speed, from among a plurality of golf clubs (hereinafter, candidate clubs) belonging to the optimal weight range specified in the optimal index specification process will be described. The optimal club is specified based on the values of grip end moment of inertia $I_G$ and swing moment of inertia $I_S$ in the case where the golfer 7 who is undergoing fitting uses each of the candidate clubs.

Note that grip end moment of inertia $I_G$ is the moment of inertia about the grip end, and is calculated as $I_G = I_2 + m_2 L^2$. On the other hand, swing moment of inertia $I_S$ is the moment of inertia about the shoulder during the swing, and can be calculated in accordance with the following equation.

$$I_S = I_2 + m_2(2r+L)^2 + I_1 + m_1 r^2$$

Note that the weight of the arm of each golfer 7 remains the same, even if different golf clubs are used. Accordingly, for ease of understanding, swing moment of inertia $I_S$ in the present embodiment is defined in accordance with the following equation, omitting the rotational part of the moment of inertia of the arm.

$$I_S = I_2 + m_2(2r+L)^2$$

Figure 21:
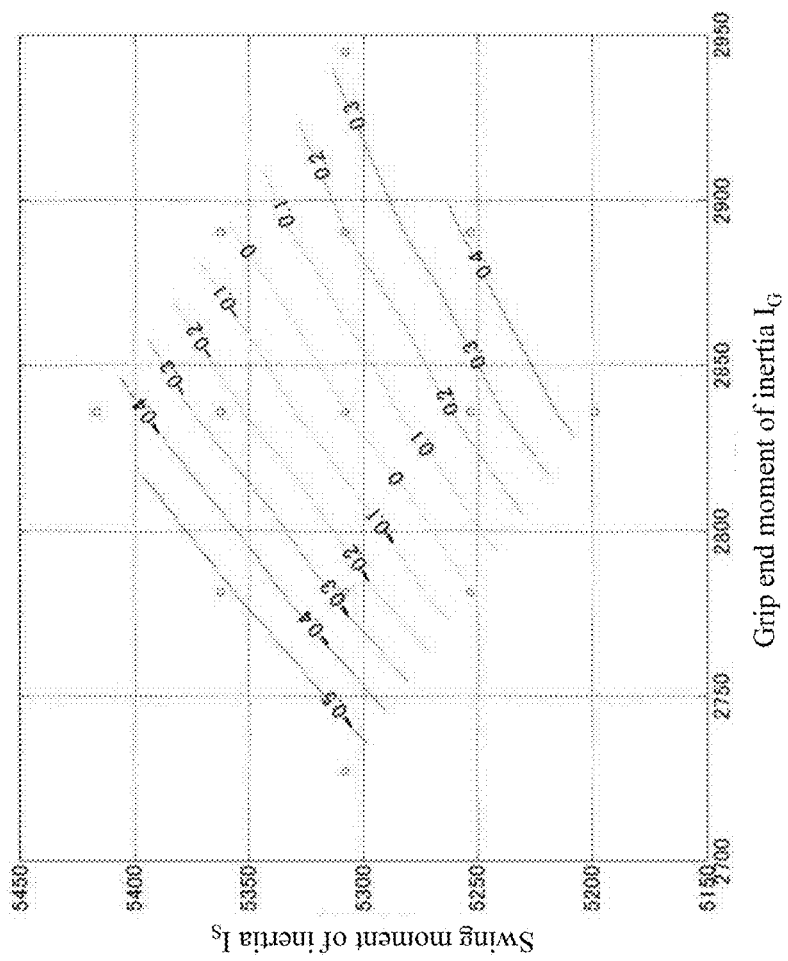
FIG. 21 is a contour diagram of head speed derived through simulation.
Figure 22:
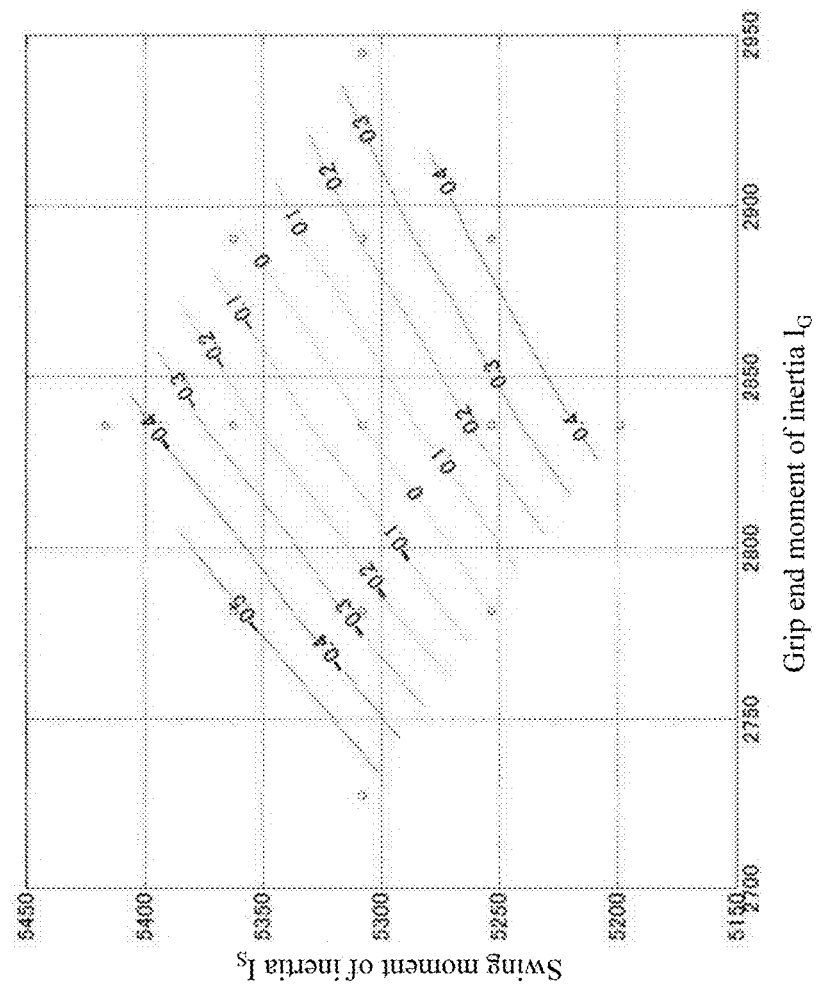
FIG. 22 is a contour diagram of head speed derived through another simulation.
Figure 23:
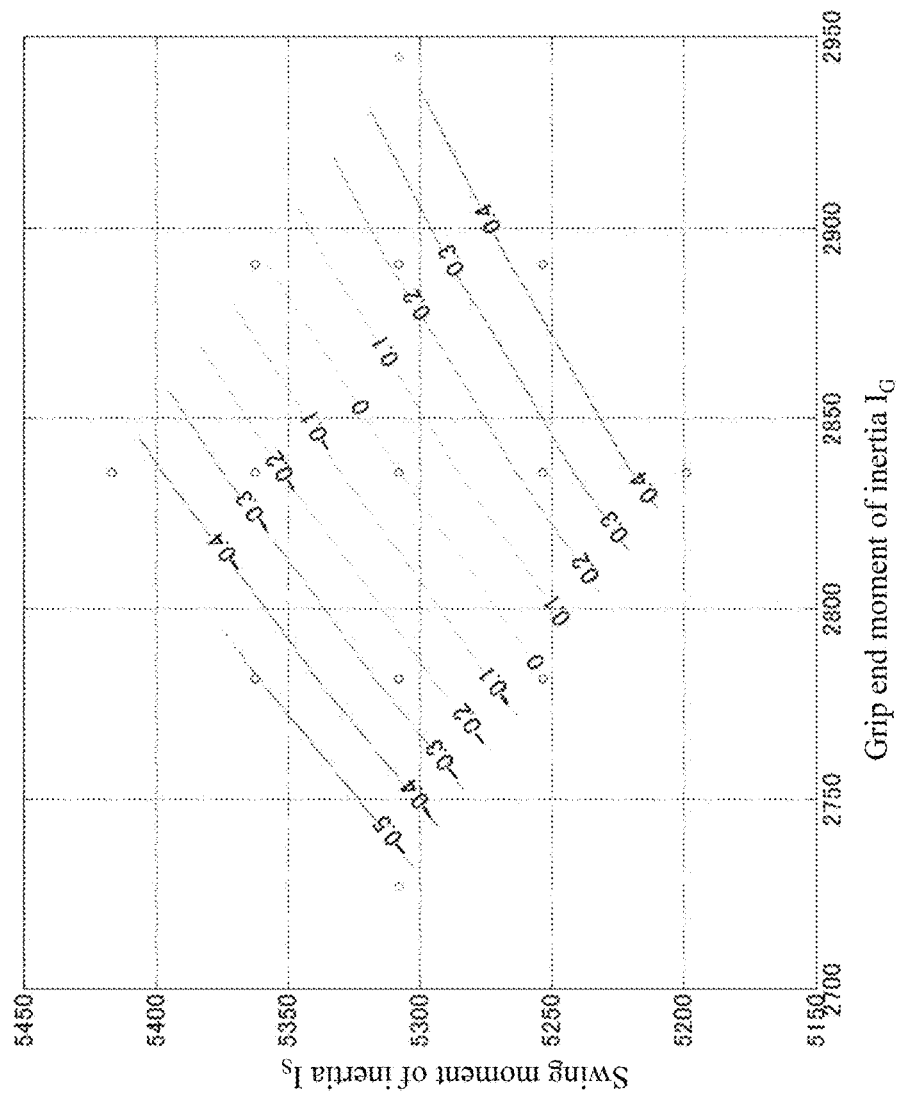
FIG. 23 is a contour diagram of head speed derived through yet another simulation.

The algorithm of the optimal club specification process described below is based on head speed $V_h$, grip end moment of inertia $I_G$ and swing moment of inertia $I_S$ having a relationship such as shown in FIGS. 21 to 23. FIGS. 21 to 23 show the results of simulations performed by the inventors. The 13 dots (circles) in an $I_G$–$I_S$ plane in FIG. 21 are dots showing $(I_G, I_S)$ when a subject swings 13 golf clubs having different specifications. Note that this data is not data obtained by getting the subject to actually take practice hits with 13 golf clubs, but data obtained by getting the subject to take practice hits with one golf club (hereinafter, reference club) and performing simulation based on the data measured at this time.

The specifications (golf club weight $m_2$[g], center-of-gravity distance L [mm], moment of inertia $I_2$ [kg·cm²]) of the reference club were (272, 936, 453). Also, a sensor unit 1 such as used in the measurement process was attached to the reference club. The subject was then made to take practice hits with the reference club, inverse kinetic analysis was performed in accordance with a similar algorithm to the abovementioned algorithm, and torque $T_1$ about the shoulder, torque $T_2$ about the grip 42 and arm length R were calculated. Next, forward kinetic analysis was performed using the values of the specifications (golf club weight $m_2$, center-of-gravity distance L, moment of inertia $I_2$, etc.) of the 13 golf clubs, assuming that the parameters $T_1$, $T_2$ and R are constant. Note that, in the simulation of FIG. 21, golf clubs having a golf club weight $m_2$ of 272 g (constant) were used, and the specifications (L, $I_2$) of the 12 remaining golf clubs excluding the reference club, were (941, 192), (941, 138), (938.5, 324), (936, 507), (941, 83), (938.5, 270), (933.5, 633), (931, 809), (936, 399), (933.5, 578), (931, 755) and (931, 700). Head speed $V_h$, grip end moment of inertia $I_G$, and swing moment of inertia $I_S$ of each golf club were calculated using the above forward kinetic analysis. The ten diagonal lines drawn in FIG. 21 are the contour lines of head speed $V_h$ derived based on the values of 13 head speeds $V_h$.

The results of having performed similar simulation on 13 different golf clubs are shown in FIGS. 22 and 23. Specifically, in the simulation of FIG. 22, golf clubs having a center-of-gravity distance L of 936 cm (constant) were used, and the specifications ($m_2$, $I_2$) of the 12 remaining golf clubs excluding the reference club were (284, 349), (284, 294), (278, 400), (272, 507), (284, 240), (278, 346), (266, 560), (260, 666), (272, 399), (266, 506), (260, 612) and (260, 557). Also, in the simulation of FIG. 23, golf clubs having an moment of inertia $I_2$ of 453 kg·cm² (constant) were used, and the specifications (L, $m_2$) of the 12 remaining golf clubs excluding the reference club were (932.6, 293), (930.9, 297), (934.3, 282), (937.8, 267.6), (929.2, 302), (932.5, 287), (933.5, 258), (943.5, 244), (934.2, 276.4), (937.8, 262), (941.5, 248) and (939.7, 252).

The contour diagrams in FIGS. 21 to 23 are drawn at 0.1 m/s intervals. The numerical values attached to these contour lines are the values of relative head speeds $V_h$ when head speed $V_h$ of the reference club is taken as 0.0 m/s. It is evident from these contour diagrams that, in the $I_G$–$I_S$ plane, head speed $V_h$ improves downward to the right and drops upward to the left. In other words, it is evident that head speed $V_h$ improves as the value of swing moment of inertia $I_S$ decreases and the value of grip end moment of inertia $I_G$ increases. This tendency is not dependent on conditions such as the golf club weight $m_2$ being constant, center-of-gravity distance L being constant or moment of inertia $I_2$ being constant.

Incidentally, it is generally thought that when grip end moment of inertia $I_G$ and swing moment of inertia $I_S$ increase, the golf club becomes more difficult to swing since the position of the center of gravity approaches the head, causing a drop in head speed $V_h$. However, the inventors noticed from the simulation results of FIGS. 21 to 23 that, even given an increase in swing moment of inertia $I_G$, for example, head speed $V_h$ can actually be improved if the increase in grip end moment of inertia $I_S$ relative to this increase in swing moment of inertia $I_G$ is at or below a given value. Further investigation by the inventors revealed that this can be explained from the results of different simulation shown in FIG. 24.

Figure 24:
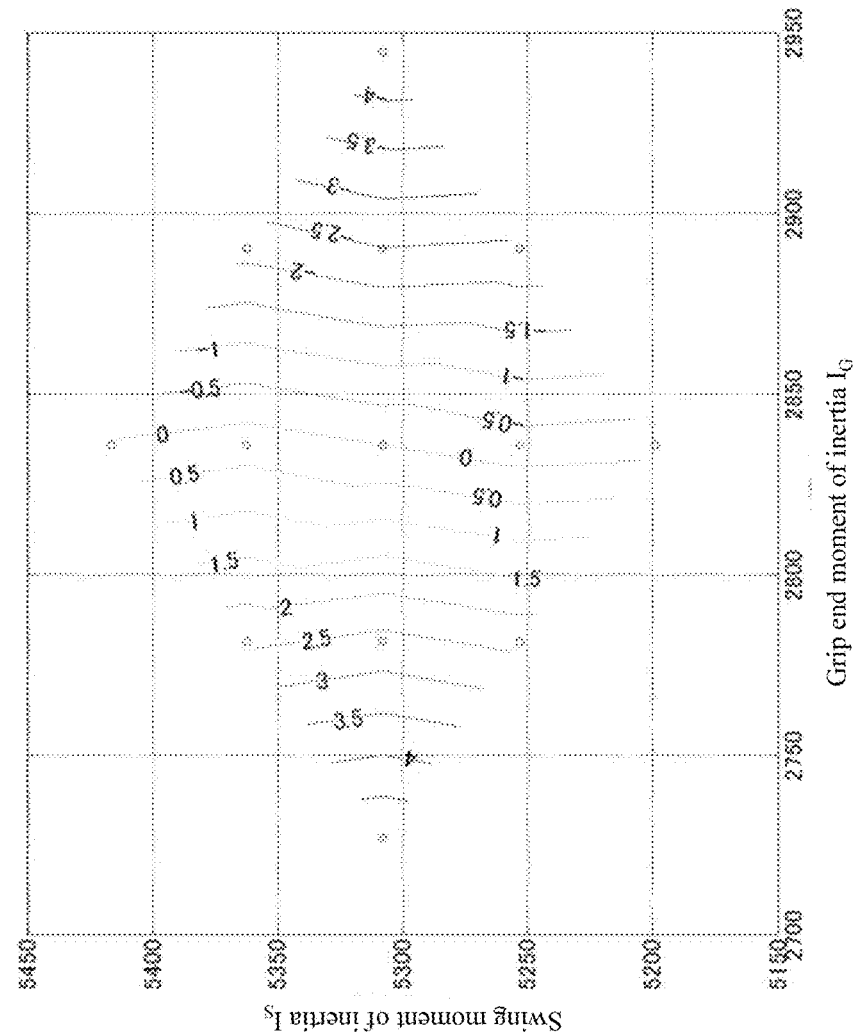
FIG. 24 is a contour diagram of wrist-cock angles derived through simulation.

FIG. 24 is a contour diagram of wrist-cock angles derived based on the values of 13 wrist-cock angles at the time of the subject swinging the 13 golf clubs in the simulation of FIG. 21. Note that a wrist-cock angle as referred to here is the angle formed by the arm and the golf club at wrist-cock release timing $t_r$ (angle shown in FIG. 11 with a dashed-dotted line).

The contour lines in FIG. 24 are drawn at 0.5 degree intervals. The numerical values attached to these contour lines are relative angles when the wrist-cock angle of the reference club is taken as 0.0 degrees. It is evident from these contour diagrams that, in the $I_G$–$I_S$ plane, the wrist-cock angle becomes smaller towards the right and becomes larger towards the left. In other words, it is evident that the wrist-cock angle becomes smaller as grip end moment of inertia $I_G$ increases. On the other hand, given that the contour lines roughly extend vertically up and down, the wrist-cock angle is not affected by swing moment of inertia $I_S$. Note that, for ease of description, only the results of the simulation corresponding to FIG. 21 are shown, but a similar tendency regarding the wrist-cock angle was confirmed in the simulations corresponding to FIGS. 22 and 23.

Also, a small wrist-cock angle means that the wrist cock is being held and the golf club passes close to the golfer's body during the swing. Accordingly, in the case where the wrist-cock angle is small, the effectual swing moment of inertia $I_S$ decreases and an increase in head speed $V_h$ can be expected.

It is evident from the above that even when grip end moment of inertia $I_G$ increases, if the increase in swing moment of inertia $I_S$ is at or below a fixed value, the advantage gained from the wrist-cock angle being small outweighs the disadvantage of the golf club becoming more difficult to swing, and head speed $V_h$ improves. That is, head speed $V_h$ can be improved if grip end moment of inertia $I_G$ can be increased and swing moment of inertia $I_S$ can be reduced.

The optimal club specification process is executed based on the above findings. First, the optimal club specification unit 124E narrows down the candidate clubs from among the plurality of golf clubs that are targeted for fitting (hereinafter, target clubs). Specifically in the storage unit 23, information showing the specifications of each target club (hereinafter, specification information) is stored in advance. In the present embodiment, values such as golf club weight $m_2$, moment of inertia $I_2$ about the center of gravity of the golf club 4, and distance (center-of-gravity distance) L from the grip 42 to the center of gravity of the golf club 4 are stored with respect to each target club as specifications as referred to here. Accordingly, the optimal club specification unit 124E specifies all the golf clubs belonging to the optimal weight range as candidate clubs from among the target clubs, by referring to the specification information in the storage unit 23. Note that in the case where there is only one candidate club, the following processing is omitted and that one candidate club is specified as the optimal club.

On the other hand, if there are a plurality of candidate clubs, the optimal club, being the golf club that can particularly increase head speed, is specified from among these candidate clubs. Specifically, the optimal club specification unit 124E derives grip end moment of inertia $I_G$ and swing moment of inertia $I_S$ that occurred at the time that the golfer 7 who is undergoing fitting swung each of the candidate clubs, in accordance with the abovementioned definitional equation. At this time, forward kinetic analysis is executed using a parameter R that has already been calculated in processes from the measurement process to the optimal index specification process and the values of specifications (golf club weight $m_2$, center-of-gravity distance L, moment of inertia $I_2$, etc.) of the candidate clubs. In this case, the golfer 7 does not need to swing the candidate clubs again.

Figure 25C:
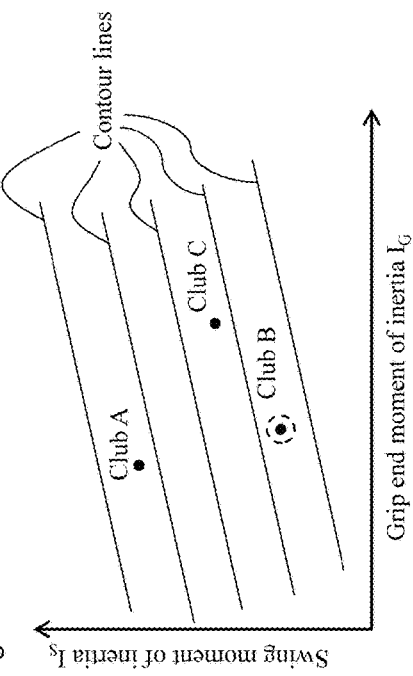
FIGS. 25A to 25C are diagrams illustrating an optimal club specification process.
Figure 25B:
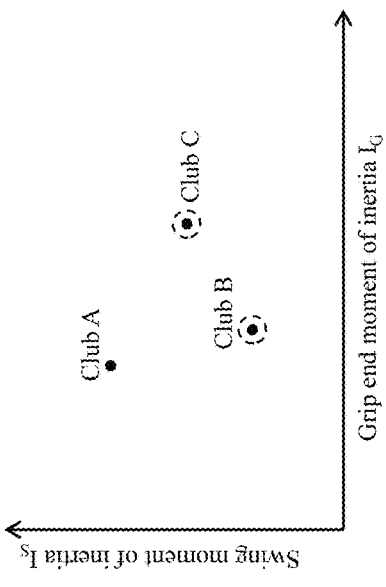
Figure 25A:
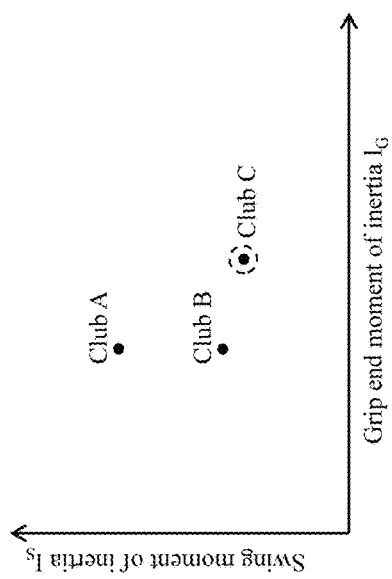

When moments of inertia $I_G$ and $I_S$ corresponding to each candidate club become known, the optimal club specification unit 124E specifies the golf club having both the smallest swing moment of inertia $I_S$ and the largest grip end moment of inertia $I_G$, from among the plurality of candidate clubs, and takes this golf club as the optimal club. Specifically, the optimal club specification unit 124E plots the points of ($I_G$, $I_S$) corresponding to each candidate club in an $I_G$–$I_S$ plane, and determines that the candidate club corresponding to the most lower right point to be the optimal club. For example, in the case where three candidate clubs A, B and C such as shown in FIG. 25A exist, the candidate club C is determined to be the optimal club. On the other hand, in the case where three candidate clubs A, B and C such as shown in FIG. 25B exist, it cannot be determined which of the candidate clubs B and C is the most lower right. In this case, both B and C are judged as optimal clubs.

Note that the relative merits of the plurality of candidate clubs corresponding to B and C in FIG. 25B can also be judged if contour lines such as shown in FIGS. 21 to 23 can be drawn in the $I_G$–$I_S$ plane. Accordingly, in another embodiment, a configuration may be adopted in which the optimal club specification unit 124E derives the contour line of head speed $V_h$ in the $I_G$–$I_S$ plane through forward kinetics analysis, using parameters $T_1$, $T_2$ and R that have already been calculated, and the values of various predetermined specifications (golf club weight $m_2$, center-of-gravity distance L, moment of inertia $I_2$, etc.) of golf clubs. Note that this contour line is dependent on the golfer 7. the relative levels of head speeds $V_h$ corresponding to a plurality of candidate clubs such as B and C can then be determined (see FIG. 25C) from the slope of this contour line, and the candidate club having the highest head speed $V_h$ can be judged to be the optimal club.

When the above processing has ended, the display control unit 124D displays information specifying the optimal club on the display unit 21. The golfer 7 can thereby comprehend the optimal golf club for himself or herself. The display control unit 124D is also able to combine display of the graphs shown in FIGS. 25A to 25C on the display unit 21, in order to improve the persuasiveness of the output values.

3. Modifications

Although a number of embodiments of the present invention have been described above, the present invention is not limited to the above embodiments, and variations that do not depart from the gist of the invention are possible. For example, the following variations are possible. Also, the substance of the following modifications can be combined as appropriate.

3-1. In the first and second embodiments, a sensor unit 1 having three sensors, namely, an acceleration sensor, an angular velocity sensor and a geomagnetic sensor, was used as the measurement device that measures the swing action of the golfer 7, but other configurations of the measurement device can also be adopted. For example, the geomagnetic sensor can be omitted. In this case, it is possible to use a statistical technique to change the measurement data from the xyz local coordinate system to the XYZ global coordinate system. Note that since such techniques are well-known technologies (if needed, see JP 2013-56074A), detailed description thereof will be omitted here. Alternatively, a three-dimensional measurement camera can be used as the measurement device. Since techniques for measuring the behavior of golfers, golf clubs and golf balls using a three-dimensional measurement camera are also well-known, detailed description thereof will be omitted here. Note that, in the case where a three-dimensional measurement camera is used, the transformation process from the xyz local coordinate system to the XYZ global coordinate system of measurement data can be omitted, and the behavior of the grip in the XYZ global coordinate system can be directly measured.

3-2. In the first and second embodiments, head speed $V_h$ was calculated based on a multiple regression equation that uses wrist-cock release timing $t_r$ and average power $E_{1\_AVE}$ as explanatory variables, but can also be calculated by other methods. For example, a configuration may be adopted in which head speed $V_h$ is calculated based on a multiple regression equation that includes at least one of wrist-cock release timing $t_r$ during the swing, energy exertion amount $E_1$ and average power $E_{1\_AVE}$ as an explanatory variable. It is, of course, possible to use all of these three parameters as explanatory variables.

Also, head speed $V_h$ may be geometrically calculated in accordance with the following equation, rather than with a statistical technique that is based on a multiple regression equation. Note that $L_{club}$ is the length of the golf club, which is a specification of the golf club. Head speed $V_h$ can also be directly measured using a measurement device composed of a camera or the like.

Position Vector ($d_{hX}$, $d_{hY}$) of Head at Distal End of Shaft 40

$$d_{hX} = 2X_1 + L_{club} \cos \theta_2$$

$$d_{hY} = 2Y_1 + L_{club} \sin \theta_2$$

Velocity Vector ($V_{hX}$, $V_{hY}$) of Head at Distal End of Shaft 40

$$V_{hX} = 2V_{X1} - L_{club}\omega_2 \sin \theta_2$$

$$V_{hY} = 2V_{Y1} + L_{club}\omega_2 \cos \theta_2$$

$$V_h = \text{sqrt}(V_{hX}^2 + V_{hY}^2)$$

3-3. The swing indices shown in the first and second embodiments are illustrative, and various other swing indices can be calculated based on the calculated movement of the pseudo shoulder. For example, the following indices are conceivable.

(1) A head speed other than the timing of impact (2) A torque exertion amount, an average torque, an average power and an energy exertion amount (or an arbitrary combination thereof) of arbitrary regions of the shoulders, the arms, the grip 42 and the golf club 4, without being limited to the examples in the first and second embodiments.

(3) A torque exertion amount, average torque, average power, and energy exertion amount in an appropriate segment during the swing, without being limited to the segments of the first and second embodiments.

3-4. The swing indices are not limited to use in the above-mentioned fitting, and can be used in various applications such as golf club product development and improving a golfer's swing action.

3-5. In the second embodiment, optimal weight $m_{op}$ of the golf club 4 was calculated based on head speed $V_h$, but a relationship such as shown in FIGS. 13A and 13B holds, even between swing indices other than head speed $V_h$ and swingability indices other than weight $m_2$ of the golf club 4. Specifically, the abovementioned energy exertion amounts E and $E_1$ and average powers $E_{AVE}$ and $E_{1\_AVE}$ can be used as swing indices for calculating an optimal swingability index, for example. Torque exertion amount $T_{ti}$ and average torque $T_{AVE}$ which will be described below can also be used as swing indices. Note that energy exertion amounts E and $E_1$ and average powers $E_{AVE}$ and $E_{1\_AVE}$ are applicable to the model of FIG. 13A, and torque exertion amount $T_{ti}$ and average torque $T_{AVE}$ can be applied to a model as shown in FIG. 13B.

Also, grip end moment of inertia $I_G$ and swing moment of inertia $I_S$ can be used as swingability indices. Note that the swing indices and the swingability indices described herein can be arbitrarily combined.

Also, in the case where grip end moment of inertia $I_G$ is used as the swingability index, the golf clubs 4 that are used for practice hitting in the measurement process are preferably golf clubs having an extremely large grip end moment of inertia $I_G$ and golf clubs having an extremely small grip end moment of inertia $I_G$. In this case, the difference between the extremely large grip end moment of inertia $I_G$ (the smallest if there are a plurality of clubs) and the extremely small grip end moment of inertia $I_G$ (the largest if there are a plurality of clubs) is preferably greater than or equal to 250 kg·cm², and more preferably greater than or equal to 400 kg·cm². Also, the difference in $I_G$ between two golf clubs 4 belonging to the proportional region is preferably greater than or equal to 100 kg·cm², and more preferably greater than or equal to 125 kg·cm². Also, the difference between head speed $V_h$ by two golf clubs 4 belonging to the proportional region is preferably greater than or equal to 0.8 m/s, and more preferably greater than or equal to 1.0 m/s.

Torque Exertion Amount $T_{ti}$ and Average Torque $T_{AVE}$

Torque exertion amount $T_{ti}$ is a value obtained by integrating torque $T_1$ about the shoulder in the swing period, and is, for example, calculated by integrating the segment from top to impact. $T_{ti}$ indicates the torque exertion amount that is exerted for the entire double pendulum during the swing. Note that, in calculating torque exertion amount $T_{ti}$, a configuration may be adopted in which only positive torque $T_1$ is integrated or in which the average value of torque $T_1$ is integrated. Average torque $T_{AVE}$ is the average torque per unit of time that is exerted for the entire double pendulum, and can be calculated as $T_{AVE} = T_{ti}(t_i - t_t)$, for example.

3-6. In the second embodiment, the number of the golf club 4 with which practice hits are taken in the measurement process was three but is not limited thereto. More accurate regression lines $l_1$ and $l_2$ of the swing index can also be calculated by acquiring measurement data from a large number of golf clubs 4 and plotting a large number of points that are based on this measurement data in a swing index-swingability index plane. Such regression lines $l_1$ and $l_2$ can be calculated by a method such as least-squares.

The number of the golf club 4 with which practice hits are taken in the measurement process can also be set to two. That is, it is possible to calculate first regression line $l_1$ based on the measurement data from one golf club 4, and to calculate second regression line $l_2$ based on the measurement data from one golf club 4.

To be specific, the inventors confirmed, in analysis based at least on the relationship between head speed $V_h$ and golf club weight $m_2$, that the slope of second regression line $l_2$ is correlated with each of wrist-cock release timing $t_r$ and head speed $V_h$. Accordingly, the slope of second regression line $l_2$ can be represented by a regression equation that uses wrist-cock release timing $t_r$ and/or head speed $V_h$ as explanatory variables. That is, a slope u of regression line $l_2$ in the proportional region can be calculated by the following equation (in the case where both $t_r$ and $V_h$ are used as explanatory variables).

$$u = w_1 \cdot t_r + w_2 \cdot V_h + w_3$$

Coefficients $w_1$, $w_2$ and $w_3$ can be calculated by multiple regression analysis from a large amount of test data. Also, in calculating coefficients $w_1$, $w_2$ and $w_3$ based on multiple regression analysis, coefficients $w_1$, $w_2$ and $w_3$ can also be calculated for each layer by stratifying test subjects based on head speed $V_h$ or the like.

In the case where the slope of second regression line $l_2$ is derived as described above, second regression line $l_2$ can be calculated as a straight line that has that slope and passes through points corresponding to a swing index that is based on measurement data.

3-7. In the second embodiment, first regression line $l_1$ was a straight line parallel to the axis of the swingability index, but may be a straight line having a slope. This is because the swing index may change gently relative to the swingability index (may become roughly constant), as shown in the test data of FIG. 19. In this case, processing such as measuring the measurement data of a plurality of golf clubs 4 can also be performed to calculate first regression line enabling first regression line $l_1$ to be specified with a similar method to second regression line $l_2$.

REFERENCE SIGNS LIST

1 Sensor unit (measurement device)
2 Golf swing analysis apparatus
3 Golf swing analysis program
4 Golf club
7 Golfer
24A Acquisition unit (input unit , receiver)
24B Grip behavior derivation unit
24C Shoulder behavior derivation unit
24D Index calculation unit
41 Head
42 Grip
100 Golf swing analysis system
101 Fitting system
102 Fitting apparatus
103 Fitting program
124A Acquisition unit
124B Index calculation unit
124C Optimal index specification unit

The invention claimed is:

1. A golf swing analysis apparatus for analyzing a swing action of a golf club, comprising:
a communication device;
a storage;
an acquisition unit of a processor configured to acquire a measurement value obtained by measuring the swing action using a measurement device from the measurement device via the communication device and store the measurement value in the storage;
a grip behavior derivation unit of the processor configured to derive a behavior of a grip of the golf club that occurs during the swing action, based on the measurement value stored in the storage; and
a shoulder behavior derivation unit of the processor configured to derive a behavior of a pseudo shoulder of a golfer that occurs during the swing action, based on the behavior of the grip, the behavior of the pseudo shoulder including a rotary motion of the pseudo shoulder,
wherein the grip behavior derivation unit is configured to derive the behavior of the grip in a global coordinate system, and transform the derived behavior of the grip into a behavior in a swing plane, and
wherein the shoulder behavior derivation unit is configured to derive the behavior of the pseudo shoulder in the swing plane, based on the behavior of the grip in the swing plane.

2. The golf swing analysis apparatus according to claim 1, wherein the grip behavior derivation unit is configured to derive a grip velocity and a grip angular velocity, and
the shoulder behavior derivation unit is configured to calculate an angular velocity of an arm of the golfer, based on the grip velocity.

3. The golf swing analysis apparatus according to claim 1, wherein the shoulder behavior derivation unit is configured to derive the behavior of the pseudo shoulder, under an assumption that the grip circulates about the shoulder and the shoulder does not move during the swing action.

4. The golf swing analysis apparatus according to claim 1, wherein the acquisition unit is configured to acquire the measurement value of the swing action measured by an acceleration sensor and an angular velocity sensor attached to the golf club that serve as the measurement device.

5. The golf swing analysis apparatus according to claim 1, further comprising an index calculation unit configured to calculate at least one of a head speed, a torque exertion amount, an average torque, an average power and an energy exertion amount, as a swing index characterizing the swing action, based on the behavior of the grip and the behavior of the pseudo shoulder.

6. A golf swing analysis method of using the golf swing analysis apparatus according to claim 1 for analyzing a swing action of a golf club, comprising the steps of:
measuring the swing action using the measurement device to acquire the measurement value;
deriving the behavior of the grip of the golf club that occurs during the swing action, based on the measurement value of the swing action; and
deriving the behavior of the pseudo shoulder of the golfer that occurs during the swing action, based on the behavior of the grip,
wherein the step of deriving of the behavior of the grip includes deriving the behavior of the grip in the global coordinate system, and transforming the derived behavior of the grip into the behavior in the swing plane, and
wherein the step of deriving of the behavior of the pseudo shoulder includes deriving the behavior of the pseudo shoulder in the swing plane, based on the behavior of the grip in the swing plane.

7. The golf swing analysis apparatus according to claim 1, wherein the pseudo shoulder is a shoulder of an arm of the golfer, the arm holding the golf club.

8. A golf swing analysis apparatus for analyzing a swing action of a golf club, comprising:
a communication device;
a storage;
an acquisition unit of a processor configured to acquire a measurement value obtained by measuring the swing action using a measurement device from the measurement device via the communication device and store the measurement value in the storage;
a grip behavior derivation unit of the processor configured to derive a behavior of a grip of the golf club that occurs during the swing action, based on the measurement value stored in the storage; and
a shoulder behavior derivation unit of the processor configured to derive a behavior of a pseudo shoulder of a golfer that occurs during the swing action, based on the behavior of the grip, the behavior of the pseudo shoulder including a rotary motion of the pseudo shoulder,
wherein the acquisition unit is configured to acquire the measurement value of the swing action measured by an acceleration sensor, an angular velocity sensor and a geomagnetic sensor attached to the golf club that serves as the measurement device.

9. A golf swing analysis method of using the golf swing analysis apparatus according to claim 8 for analyzing a swing action of a golf club, comprising the steps of:
measuring the swing action using the measurement device to acquire the measurement value;
deriving the behavior of the grip of the golf club that occurs during the swing action, based on the measurement value of the swing action; and
deriving the behavior of the pseudo shoulder of the golfer that occurs during the swing action, based on the behavior of the grip, wherein the step of measuring includes acquiring the measurement value of the swing action measured by the acceleration sensor, the angular velocity sensor and the geomagnetic sensor attached to the golf club that serve as the measurement device.

10. The golf swing analysis apparatus according to claim 8, wherein the pseudo shoulder is a shoulder of an arm of the golfer, the arm holding the golf club.

11. A golf swing analysis apparatus for analyzing a swing action of a golf club, comprising:
   a communication device;
   a storage;
   an acquisition unit of a processor configured to acquire a measurement value obtained by measuring the swing action using a measurement device from the measurement device via the communication device and store the measurement value in the storage;
   a grip behavior derivation unit of the processor configured to derive a behavior of a grip of the golf club that occurs during the swing action, based on the measurement value stored in the storage;
   a shoulder behavior derivation unit of the processor configured to derive a behavior of a pseudo shoulder of a golfer that occurs during the swing action, based on the behavior of the grip, the behavior of the pseudo shoulder including a rotary motion of the pseudo shoulder; and
   an index calculation unit of the processor configured to calculate a value of a wrist-cock release timing that occurs during the swing action, an average power and/or an energy exertion amount, based on the behavior of the grip and the behavior of the pseudo shoulder, and calculate a head speed that occurs at a time of impact as a swing index characterizing the swing action, in accordance with a predetermined regression equation that uses the wrist-cock release timing, the average power and/or the energy exertion amount as explanatory variables.

12. A golf swing analysis method of using the golf swing analysis apparatus according to claim 11 for analyzing a swing action of a golf club, comprising the steps of:
   measuring the swing action using the measurement device to acquire the measurement value;
   deriving the behavior of the grip of the golf club that occurs during the swing action, based on the measurement value of the swing action;
   deriving the behavior of the pseudo shoulder of the golfer that occurs during the swing action, based on the behavior of the grip;
   calculating the value of the wrist-cock release timing that occurs during the swing action, the average power and/or the energy exertion amount, based on the behavior of the grip and the behavior of the pseudo shoulder; and
   calculating the head speed that occurs at the time of impact as the swing index characterizing the swing action, in accordance with the predetermined regression equation that uses the wrist-cock release timing, the average power and/or the energy exertion amount as explanatory variables.

13. The golf swing analysis apparatus according to claim 11, wherein the pseudo shoulder is a shoulder of an arm of the golfer, the arm holding the golf club.

* * * * *